(12) United States Patent
Suzuki et al.

(10) Patent No.: US 9,545,343 B2
(45) Date of Patent: Jan. 17, 2017

(54) ABSORBENT ARTICLE HAVING A LIQUID-IMPERMEABLE INDIVIDUAL-WRAPPING SHEET WITH A LIQUID-STORING PORTION AT A TIME OF USE

(75) Inventors: Migaku Suzuki, Tokyo (JP); Yoshio Hirai, Tokyo (JP)

(73) Assignee: DAIO PAPER CORPORATION, Shikokuchuo-Shi (JP)

( * ) Notice: Subject to any disclaimer, the term of this patent is extended or adjusted under 35 U.S.C. 154(b) by 825 days.

(21) Appl. No.: 13/371,841

(22) Filed: Feb. 13, 2012

(65) Prior Publication Data
US 2013/0211359 A1 Aug. 15, 2013

(51) Int. Cl.
*A61F 13/15* (2006.01)
*A61F 13/20* (2006.01)
*A61F 13/551* (2006.01)

(52) U.S. Cl.
CPC ....... *A61F 13/5514* (2013.01); *A61F 13/5515* (2013.01)

(58) Field of Classification Search
CPC ............ A61F 13/51478; A61F 13/5148; A61F 13/5513; A61F 13/5514; A61F 13/5515; A61F 2013/51468–2013/51482; A61F 2013/55155; A61F 2013/55195
USPC ............ 604/385.01, 385.02, 385.13, 385.19, 604/385.28
See application file for complete search history.

(56) References Cited

U.S. PATENT DOCUMENTS

| | | | |
|---|---|---|---|
| 3,973,567 A * | 8/1976 | Srinivasan et al. | 604/385.05 |
| 4,402,689 A * | 9/1983 | Baum | 604/387 |
| 4,846,828 A * | 7/1989 | Mendelsohn | 604/387 |
| 4,857,066 A * | 8/1989 | Allison | 604/385.13 |
| 5,037,418 A * | 8/1991 | Kons et al. | 604/387 |
| 5,478,336 A * | 12/1995 | Pigneul | 604/385.04 |
| 5,569,228 A * | 10/1996 | Byrd et al. | 604/385.02 |

(Continued)

FOREIGN PATENT DOCUMENTS

| | | | |
|---|---|---|---|
| EP | 1 470 806 A1 * | 10/2004 | A61F 5/44 |
| JP | A-11-347066 | 12/1999 | |

(Continued)

OTHER PUBLICATIONS

Translation of Jun. 10, 2013 Office Action issued in Japanese Patent Application No. 2009-177749.

*Primary Examiner* — Michele M Kidwell
(74) *Attorney, Agent, or Firm* — Oliff PLC

(57) ABSTRACT

Disclosed is an absorbent article, having an individual-wrapping sheet which is liquid-impermeable; an absorber arranged on an upper side of the individual-wrapping sheet, containing super absorbent polymer, and capable of absorbing an aqueous liquid; and a back-up sheet arranged between the individual-wrapping sheet and the absorber and capable of retaining the aqueous liquid, in which the individual-wrapping sheet has a liquid-storing portion in a form of bag which is provided in a rear portion of the individual-wrapping sheet and forms an internal space on the upper side of the individual-wrapping sheet, and in which a rear end portion of the absorber exists in the internal space formed by the liquid-storing portion. By using this absorbent article, a material used for individual wrapping can be utilized at the time of wearing the absorbent article without disposal of the material, and leakage is less liable to occur.

19 Claims, 21 Drawing Sheets

(56) References Cited

U.S. PATENT DOCUMENTS

| | | | |
|---|---|---|---|
| 6,669,676 B1* | 12/2003 | Gause | 604/385.02 |
| 6,896,668 B2* | 5/2005 | Kashiwagi et al. | 604/385.02 |
| 8,540,690 B2* | 9/2013 | Nomoto et al. | 604/385.04 |
| 8,858,521 B2* | 10/2014 | Karsenti | 604/385.02 |
| 2003/0004484 A1 | 1/2003 | Hammons et al. | |
| 2005/0015067 A1* | 1/2005 | Suzuki et al. | 604/385.02 |
| 2005/0033258 A1 | 2/2005 | Suzuki et al. | |
| 2011/0208148 A1* | 8/2011 | Chicoine et al. | 604/385.02 |

FOREIGN PATENT DOCUMENTS

| | | |
|---|---|---|
| JP | A-2003-180722 | 7/2003 |
| JP | A-2003-190211 | 7/2003 |
| JP | A-2003-527929 | 9/2003 |
| JP | A-2011-030638 | 2/2011 |
| WO | WO 02/090106 A1 | 11/2002 |

\* cited by examiner (A)

(B)

(C)

(D)

(A)

(B)

(A)

(B)

(A)

(B)

(A)

(B)

ABSORBENT ARTICLE HAVING A LIQUID-IMPERMEABLE INDIVIDUAL-WRAPPING SHEET WITH A LIQUID-STORING PORTION AT A TIME OF USE

BACKGROUND OF THE INVENTION

1. Field of the Invention

The present invention relates to an absorbent article.

2. Description of the Related Art

Conventionally, in the field of an absorbent article, sanitary managements of sanitary napkins, incontinence pads, and the like are particularly important. Thus, in many cases, such sanitary goods are provided to consumers under a state in which an absorbent article is individually wrapped. Such individually-wrapped absorbent articles are excellent in terms of sanitation, but bags used for individual wrapping are disposed of as trash after unpacking the absorbent articles, and hence there is a problem of trash generation.

In order to prevent such trash generation, there have been made attempts to utilize a material used for individual wrapping at the time of wearing sanitary goods without disposal of the material. For example, JP 2003-180722A (Japanese Patent Application Laid-open No. 2003-180722) describes an absorbent product including: an individual-wrapping sheet; an absorbent superimposed on the individual-wrapping sheet; a trap sheet which forms a flexible trap portion between the trap sheet and the individual-wrapping sheet, the trap portion accommodating at least one end portion of the absorbent; and a bonding tape for releasably bonding another end portion of the individual-wrapping sheet and one end portion of the individual-wrapping sheet or the trap sheet to each other so that the another end side of the individual-wrapping sheet is overlapped with the trap sheet, the bonding tape being provided to at least one of the trap sheet and the another end portion of the individual-wrapping sheet.

SUMMARY OF THE INVENTION

The trap portion of the absorbent product described in JP 2003-180722 A is provided for the purpose of temporarily storing an unabsorbed part of body fluid when a large amount of body fluid is discharged within a short period of time and a speed at which the body fluid is discharged exceeds a speed at which the body fluid is absorbed by the absorbent.

However, actually, not all of the body fluid, which has not been absorbed by the absorbent, is always stored in the trap portion. On an inner side of the individual-wrapping sheet, unabsorbed body fluid exists in other portions than the trap portion, which may cause leakage, for example, in accordance with motion of the wearer's body. In particular, when an absorbent heavily containing a super absorbent polymer (hereinafter, also referred to as "SAP") is used, such a leakage problem is serious because the SAP is characteristic in low-speed body-fluid absorption.

Therefore, the present invention has been made to achieve an object of providing an absorbent article which utilizes a material used for individual wrapping at the time of wearing without disposal of the material and which is less liable to cause leakage. Further, another object is to provide the absorbent article which has individual wrapping used for a leak preventer at the time of wearing and for wrapping at the time of disposing of after use without disposal of the material.

After careful study conducted with a view toward achieving the above-mentioned object, the inventors of the present invention have completed an absorbent article of a novel structure.

According to the present invention, there are provided the following absorbent articles according to Items (1) through (17).

(1) An absorbent article, including:

an individual-wrapping sheet which is liquid-impermeable the individual-wrapping sheet being used for a leak preventer at the time of wearing and for wrapping the absorbent article at the time of disposing of after use;

an absorber arranged on an upper side of the individual-wrapping sheet, and capable of absorbing an aqueous liquid; and a back-up sheet arranged between the individual-wrapping sheet and the absorber and capable of retaining the aqueous liquid, in which the individual-wrapping sheet has a liquid-storing portion in a form of bag which is provided in a rear portion of the individual-wrapping sheet and forms an internal space on the upper side of the individual-wrapping sheet, and in which a rear end portion of the absorber exists in the internal space formed by the liquid-storing portion.

(2) An absorbent article according to Item (1), in which the individual-wrapping sheet includes an individual-wrapping-sheet main-body portion and a pair of wing portions existing on both right and left sides of the individual-wrapping-sheet main-body portion, the pair of wing portions being coupleable to each other on any one of an upper side and a lower side of the individual-wrapping-sheet main-body portion.

(3) An absorbent article according to Item (2), in which the pair of wing portions are coupleable to each other with tackifiers applied respectively to the pair of wing portions.

(4) An absorbent article according to Item (2), in which one of the pair of wing portions includes a male member and another of the pair of wing portions includes a female member so that the pair of wing portions are coupleable to each other by fitting of the male member and the female member.

(5) An absorbent article according to Item (1), in which the individual-wrapping sheet includes, on a lower-side surface thereof, a tackifier adherable to an inner surface of an underwear garment of a wearer at a time of wearing.

(6) An absorbent article according to Item (1), in which the individual-wrapping sheet includes, on a lower-side surface thereof, an anti-slip member which suppresses slipping with respect to the inner surface of the underwear garment of a wearer at a time of wearing.

(7) An absorbent article according to Item (1), in which the individual-wrapping sheet includes, on an upper-side surface thereof, a pair of side-barrier portions standing upward, the pair of side-barrier portions being provided on both right and left sides of the individual-wrapping sheet.

(8) An absorbent article according to Item (1), in which a rear end portion of the back-up sheet exists in the internal space formed by the liquid-storing portion.

(9) An absorbent article according to Item (1), in which the back-up sheet is folded back on a rear side with respect to the rear end portion of the absorber so that a rear end portion of the back-up sheet exists on an upper side of the absorber.

(10) An absorbent article according to Item (1), in which the back-up sheet is folded back on the rear side with respect to a rear end portion of the absorber and on a front side with respect to a front end portion of the liquid-storing portion of the individual-wrapping sheet so that a rear end portion of the back-up sheet exists on an upper side of the liquid-storing portion.

(11) An absorbent article according to Item (1), in which the back-up sheet is folded back on a rear side with respect to a rear end portion of the absorber and on a front side with respect to a front end portion of the liquid-storing portion of the individual-wrapping sheet so that a rear end portion of the back-up sheet exists on a rear side with respect to the liquid-storing portion.

(12) An absorbent article according to Item (1), further including a spreading-leakage preventing sheet provided on the upper side of the absorber, the spreading-leakage preventing sheet being capable of retaining an aqueous liquid, in which a part of the spreading-leakage preventing sheet exists in the internal space of the liquid-storing portion and another part of the spreading-leakage preventing sheet is out the internal space of the liquid-storing portion.

(13) An absorbent article according to Item (12), in which the spreading-leakage preventing sheet is folded back on a front side with respect to the front end portion of the liquid-storing portion.

(14) An absorbent article according to Item (1), in which the individual-wrapping sheet is formed of a laminated body of a liquid-impermeable sheet and a hydrophobic non-woven fabric, the hydrophobic non-woven fabric existing on an upper side and/or a lower side of the liquid-impermeable sheet.

(15) An absorbent article according to Item (1), in which at least an inner surface of the individual-wrapping sheet is formed of a liquid-impermeable sheet, and in which the back-up sheet is formed of a hydrophilic non-woven fabric, the liquid-impermeable sheet and the hydrophilic non-woven fabric being formed integrally with each other as a laminated body.

(16) An absorbent article according to Item (1), which is to be used as an incontinence pad.

(17) An absorbent article according to Item (1), which is to be used as a sanitary napkin.

(18) An absorbent article, including:

an individual-wrapping sheet which is liquid-impermeable;

an absorber arranged on an upper side of the individual-wrapping sheet, and capable of absorbing an aqueous liquid; and a back-up sheet arranged between the individual-wrapping sheet and the absorber and capable of retaining the aqueous liquid, in which the individual-wrapping sheet has a liquid-storing portion in a form of bag which is provided in a rear portion of the individual-wrapping sheet and forms an internal space on the upper side of the individual-wrapping sheet, and in which a rear end portion of the absorber exists in the internal space formed by the liquid-storing portion.

According to the absorbent articles of the present invention, the material used for individual wrapping can be utilized at the time of wearing the absorbent article without disposal of the material, and leakage is less liable to occur.

DETAILED DESCRIPTION

Figure 1:
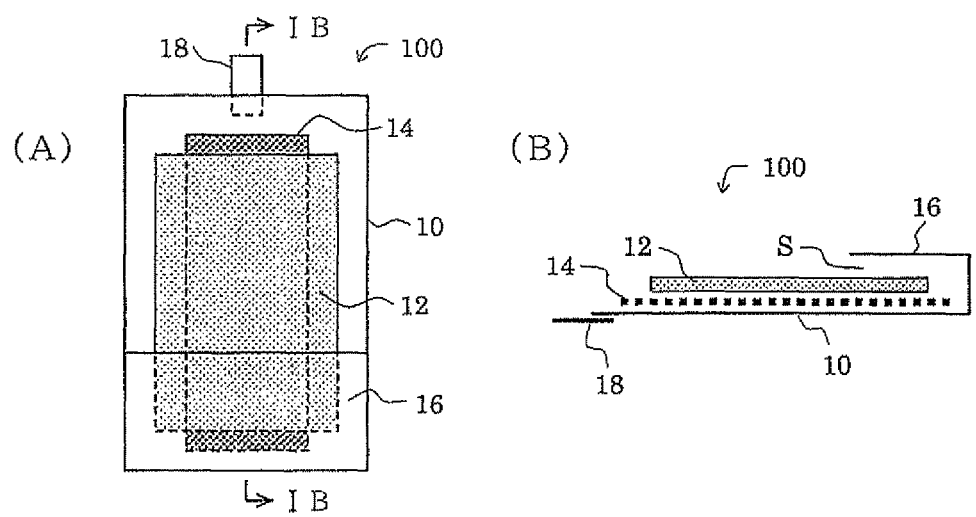
FIGS. 1A and 1B are schematic views each illustrating an example of an absorbent article according to the present invention.

Hereinafter, an absorbent article of the present invention is described in more detail based on preferred embodiment modes shown in the attached drawings. In this specification, when the absorbent article of the present invention is actually worn, a side close to a skin of a wearer is referred to as "upper" side and a side far therefrom is referred to as "lower" side. In addition, when the absorbent article of the present invention is actually worn, a side corresponding to a front side of a body of a wearer is referred to as "front" and a side corresponding to a rear side thereof is referred to as "rear". In the drawings, members which are actually in contact with each other are sometimes illustrated as being separately positioned for easy understanding. In the drawings, each of members which is illustrated by a line may have a thickness.

FIGS. 1A and 1B are schematic views each illustrating an example of the absorbent article according to the present invention. FIG. 1A is a plan view. FIG. 1B is a vertical end view taken along the line IB-IB of FIG. 1A. Note that, in each plan view of the attached drawings, the absorbent article or the like is illustrated so that the front side thereof faces upward in the view. Further, the absorbent article or the like is illustrated so that the front side thereof is arranged on the left side of each of the vertical end views of the attached drawings.

An absorbent article 100 according to the present invention basically includes an individual-wrapping sheet 10 which is liquid-impermeable, an absorber 12 which is arranged on the upper side of the individual-wrapping sheet 10, contains a super absorbent polymer, and is capable of absorbing an aqueous liquid, and a back-up sheet 14 which is arranged between the individual-wrapping sheet 10 and the absorber 12 and is capable of retaining the aqueous liquid.

The material, the structure, and the like of the individual-wrapping sheet 10 are not particularly limited as long as liquid impermeability can be secured. Examples of the individual-wrapping sheet 10 include a liquid-impermeable sheet, a laminated body of a liquid-impermeable sheet and a hydrophobic non-woven fabric (for example, highly water-resistant non-woven fabric), and a laminated body of a liquid-impermeable sheet and a hydrophilic non-woven fabric.

Examples of the liquid-impermeable sheet include a resin film made of PE, PP, PET, EVA, or the like; foamed sheets made of such resins; and a highly water-resistant non-woven fabric. A sheet having air permeability, such as an air-permeable film, is suitably used as the liquid-impermeable sheet.

Further, the individual-wrapping sheet 10 is preferably formed of a leak preventer. In this case, the individual-wrapping sheet 10 is used for a leak preventer at the time of wearing and for wrapping the absorbent article 100 at the time of disposing of after use. Additionally, the individual-wrapping sheet 10 may not be formed of a leak preventer.

In one of the preferred modes of the present invention, the individual-wrapping sheet 10 is formed of the laminated body of a liquid-impermeable sheet and a hydrophobic non-woven fabric, and the hydrophobic non-woven fabric exists on the upper side and/or the lower side of the liquid-impermeable sheet.

The mode in which the individual-wrapping sheet is formed of the laminated body of a liquid-impermeable sheet and a hydrophobic non-woven fabric and the hydrophobic non-woven fabric exists on the upper side of the liquid-impermeable sheet is preferred since that the hydrophobic non-woven fabric has a water-proof effect, and an effect of preventing body fluid from gathering and flowing in one direction is exerted due to projections and recesses formed on a surface of the hydrophobic non-woven fabric having a porous structure.

The mode in which the individual-wrapping sheet is formed of the laminated body of a liquid-impermeable sheet and a hydrophobic non-woven fabric and the hydrophobic non-woven fabric exists on the lower side of the liquid-impermeable sheet is preferred since that an excellent external appearance and an excellent feel of the absorbent article are achieved.

The mode in which the individual-wrapping sheet is formed of the laminated body of a liquid-impermeable sheet and a hydrophobic non-woven fabric and the hydrophobic non-woven fabrics exist on upper side and the lower side of the liquid-impermeable sheet has advantages of the above-mentioned two modes.

Although the individual-wrapping sheet 10 and the back-up sheet 14 of the absorbent article 100 are separate members provided independently, the absorbent article according to the present invention is not limited thereto. For example, two or more of the members, such as the individual-wrapping sheet and the back-up sheet, may be formed integrally with each other.

Specifically, for example, in one of the preferred modes of the present invention, at least an inner surface of the individual-wrapping sheet is formed of a liquid-impermeable sheet, and the back-up sheet is made of a hydrophilic non-woven fabric, the liquid-impermeable sheet and the hydrophilic non-woven fabric being formed integrally with each other as a laminated body. In this mode, when the laminated body obtained by forming the liquid-impermeable sheet and the hydrophilic non-woven fabric integrally with each other is arranged so that the hydrophilic non-woven fabric is positioned on the upper side, the hydrophilic non-woven fabric part functions as the back-up sheet, and the liquid-impermeable sheet part functions as the individual-wrapping sheet.

The individual-wrapping sheet 10 has a bag-like liquid-storing portion 16 which forms an internal space S in a rear portion on its upper side.

The liquid-storing portion 16 is formed, for example, by folding one liquid-impermeable sheet in the front-rear direction and by heat-sealing edge portions thereof through heat fusion.

The individual-wrapping sheet 10 may be formed of a plurality of members.

There are no particular limitations regarding the absorber 12 as long as it contains super absorbent polymer and is capable of absorbing body fluid. For example, it is possible to use a powder absorber such as powder wood pulp and unprocessed SAP. However, taking into consideration stability in form, risk of detachment, and the like, a sheet-like absorber is preferred. Above all, it is desired to adopt a sheet-like absorber formed by coating a non-woven fabric with super absorbent polymer.

In a preferred mode, the sheet-like absorber is a super absorbent sheet containing 50 wt % or more SAP, preferably 60 to 95 wt % SAP.

The super absorbent sheet is an ultrathin sheet-like absorber containing SAP as a main component. The super absorbent sheet has a very high SAP content, and thus is very thin. The super absorbent sheet has a thickness of preferably 1.5 mm or less, more preferably 1 mm or less.

The structure or a production process of the super absorbent sheet is not particularly limited as long as the super absorbent sheet is an ultrathin sheet-like absorber containing SAP as a main component.

An example of the super absorbent sheet may be obtained by the Air Laid process. The Air Laid process involves mixing pulverized wood pulp and SAP, adding a binder, and forming the mixture into a sheet, to thereby obtain a super absorbent sheet. Examples of the super absorbent sheet obtained by this process include NOVATHIN® (US trade name) manufactured by Rayonier Inc. and B-SAP manufactured by Oji Kinocloth Co., Ltd.

Another example of the super absorbent sheet (SAP sheet) may be obtained by a process involving coating SAP-dispersed slurry on a body fluid permeable sheet such as a non-woven fabric. The SAP-dispersed slurry is preferably prepared by dispersing SAP and microfibrillated cellulose (MFC) in a mixed solvent of water and ethanol. An example of the super absorbent sheet obtained by this process includes MEGATHIN (trade name) manufactured by Japan Absorbent Technology Institute.

Other examples of the super absorbent sheet may be obtained by a process involving applying a large amount of SAP to a raised non-woven fabric and fixing the SAP with a hot melt binder, an emulsion binder, an aqueous fiber, or the like; a process involving mixing fibrous SAP with a polyethylene terephthalate (PET) fiber and forming the mixture into a web; and providing tissues above and below an SAP layer.

The absorber may be coupled to other members such as a top sheet or side barriers. Further, as described below, still other members such as a wing may be coupled to the other members to be coupled to the absorber.

The absorber 12 is arranged on the upper side of the individual-wrapping sheet 10 so that a rear end portion thereof exists in the internal space S of the liquid-storing portion 16. With such a structure, when being discharged on the upper side of the individual-wrapping sheet 10, body fluid such as urine and blood is directly absorbed by the absorber 12. Further, even when a large amount of body fluid is discharged within a short period of time and a speed at which the body fluid is discharged exceeds a speed at which the body fluid is absorbed by the absorber 12, unabsorbed the body fluid is temporarily stored in the liquid-storing portion 16, and then absorbed by the rear end portion of the absorber 12.

Generally, an amount of body fluid discharged from a wearer is not constant but largely fluctuates, and hence a large amount of body fluid may sometimes be discharged. In addition, the absorber may be used by a wearer with urge incontinence, for example, where a large amount of urine is initially discharged despite a small total amount of urine to be discharged. Alternatively, the absorber is used only when menstrual bleeding is heavy, as exemplified by an overnight napkin.

The liquid-storing portion 16 stores body fluid when a large amount of body fluid is discharged within a short period of time as described above.

Note that, the liquid-storing portion 16 also receives droplets of the body fluid so that a periphery is not stained when the absorbent article 100 is taken off after use. In the following, description is made by way of urine as an example of the body fluid.

The back-up sheet 14 is arranged between the individual-wrapping sheet 10 and the absorber 12, and when a large amount of urine is discharged within a short period of time and a part of the urine, which has not been absorbed by the absorber 12, exists in a portion other than the liquid-storing portion 16 on the upper side of the individual-wrapping sheet 10, the back-up sheet 14 prevents urine from leaking to an outside of the absorbent article, for example, by climbing over side gathers and flowing out sidewise, or seeping from the front and rear. In other words, the back-up sheet 14 has a function of retaining the urine.

As a result of continuous careful study on causes of urine leakage, the inventors of the present invention have found out that spreading leakage rather frequently occurs.

The "spreading leakage" as used herein means leakage along the skin of a wearer, and leakage or seeping along surfaces and edge portions (for example, both side portions, front end portion, and rear end portion) of members of the absorbent article. The spreading leakage generally occurs in a small amount in a seeping manner even when the absorber of the absorbent article has a sufficient absorbing capacity. Such spreading leakage is liable to occur when unabsorbed urine in the absorbent article shifts to the left, right, front, and rear in accordance with posture and motion of the wearer.

The material for the back-up sheet 14 is not particularly limited as long as an aqueous liquid can be retained, and examples thereof include: a cotton gauze; a hydrophilic non-woven fabric such as a cellulose non-woven fabric (for example, TCF manufactured by FUTAMURA CHEMICAL CO., LTD., and BENILIESE™ manufactured by Asahi Kasei Corporation.); spun-laces such as a rayon spun-lace and a cotton spun-lace; and the above-mentioned material for the absorber 12 (for example, super absorbent sheet obtained by the Air Laid process; and super absorbent sheet obtained by the process involving coating SAP-dispersed slurry on a liquid-permeable sheet such as a non-woven fabric). Of those, in order to exert the above-mentioned function of retaining the urine, a material having a urine-absorbing speed and a urine-diffusing speed which are higher than those of the material for the absorber 12 is used as the material for the back-up sheet 14. An amount of absorbed urine per unit volume of the material for the back-up sheet 14 may be smaller than that of the material for the absorber 12. Specifically, for example, when each of the absorber 12 and the back-up sheet 14 is formed of the super absorbent sheet obtained by the process involving coating SAP-dispersed slurry on a liquid-permeable sheet such as a non-woven fabric, an SAP content of the back-up sheet 14 is set to be lower than an SAP content of the absorber 12.

The back-up sheet 14 is not particularly limited in arrangement, structure, and the like as long as at least a part of the back-up sheet 14 is arranged between the individual-wrapping sheet 10 and the absorber 12.

The back-up sheet 14 except its front end portion and rear end portion illustrated in FIGS. 1A and 1B exists between the individual-wrapping sheet 10 and the absorber 12, and the front end portion and the rear end portion respectively extend out of the absorber 12 toward the front side and the rear side. In the horizontal direction, the back-up sheet 14 exists between both sides of the absorber 12.

The rear end portion of the back-up sheet 14 exists in the internal space S of the liquid-storing portion 16. In this mode, both a urine storing function of the liquid-storing portion 16 and a urine retaining function of the back-up sheet 14 are exerted in cooperation with each other, and hence leakage is more effectively prevented. Specifically, when an amount of urine which has not been absorbed by the absorber 12 increases near a part at which urine is discharged, the unabsorbed urine is quickly retained by the back-up sheet 14, and reaches the liquid-storing portion 16 on or through the back-up sheet 14. Meanwhile, when an amount of urine which has been temporarily stored in the liquid-storing portion 16 increases, a part of the urine which has been temporarily stored in the liquid-storing portion 16 is retained after moving from the rear end portion of the back-up sheet 14 toward a center of the back-up sheet 14. In this way, the urine is prevented from overflowing from the liquid-storing portion 16, and hence leakage to be caused, for example, by motion of the wearer is effectively prevented.

The absorbent article 100 according to the present invention further includes a sealing tape 18.

One end of the sealing tape 18 is bonded to a center of the front end portion of the individual-wrapping sheet 10, and a tackifier is applied to an upper-side surface of the sealing tape 18. With this, by folding the individual-wrapping sheet 10 in two near a center in the front-rear direction thereof, the surface of the sealing tape 18 on which the tackifier is applied can be attached and detached to the liquid-storing portion 16 or a lower-side surface of the individual-wrapping sheet 10. Thus, until beginning of use of the absorbent article 100 by a wearer after being manufactured, a sanitary condition can be maintained by sealing the individual-wrapping sheet 10 in a state of being folded back. Further, the absorbent article 100 can be sanitarily disposed of after use without a need for an additional bag and the like for wrapping the absorbent article 100.

A leading end portion of the sealing tape 18 is preferred not to be applied with a tackifier. In this case, by pinching the leading end portion with fingers, the sealing tape 18 can be easily attached and detached.

Figure 2:
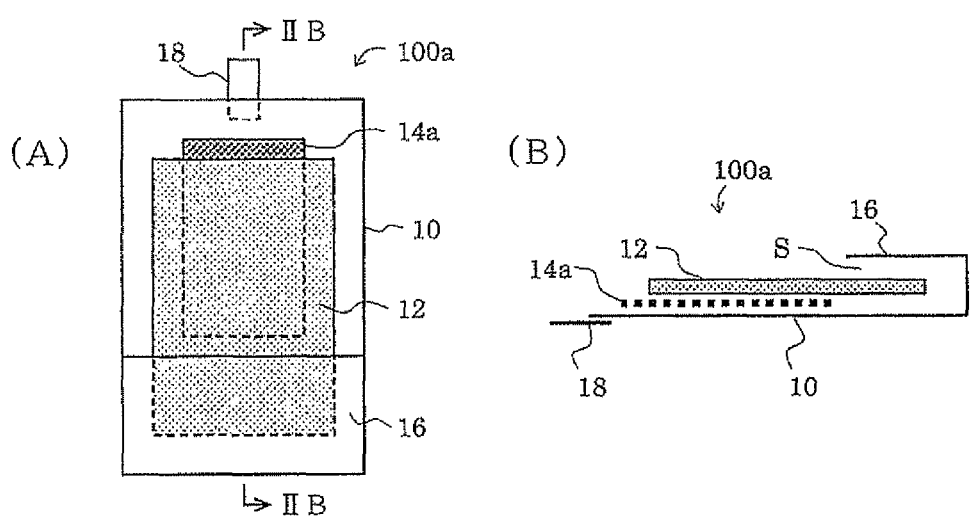
FIGS. 2A and 2B are schematic views each illustrating another example of the absorbent article according to the present invention.

FIGS. 2A and 2B are schematic views illustrating another example of the absorbent article according to the present invention. FIG. 2A is a plan view, and FIG. 2B is a vertical end view taken along the line IIB-IIB of FIG. 2A.

An absorbent article 100a illustrated in FIGS. 2A and 2B is basically the same as the absorbent article 100 except that a back-up sheet 14a exists only on a front side (in other words, rear end portion of the back-up sheet 14 does not exist in the internal space S of the liquid-storing portion 16). In this mode, urine can be retained by the back-up sheet 14a near the position at which urine is discharged. Thus, the shift of urine to the left, right, front, and rear, which may cause spreading leakage, is prevented.

Figure 3:
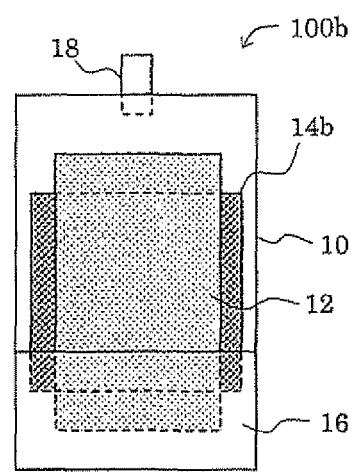
FIG. 3 is a schematic plan view illustrating still another example of the absorbent article according to the present invention.

FIG. 3 is a schematic plan view illustrating still another example of the absorbent article according to the present invention.

An absorbent article 100b illustrated in FIG. 3 is basically the same as the absorbent article 100a except that a back-up sheet 14b extends out of both sides of the absorber 12 in the horizontal direction and that a front end of the back-up sheet 14b is positioned on a rear side with respect to a front end of the absorber 12. In this mode, in comparison with the absorbent article 100a, urine can be more efficiently retained near the position at which urine is discharged.

Figure 4:
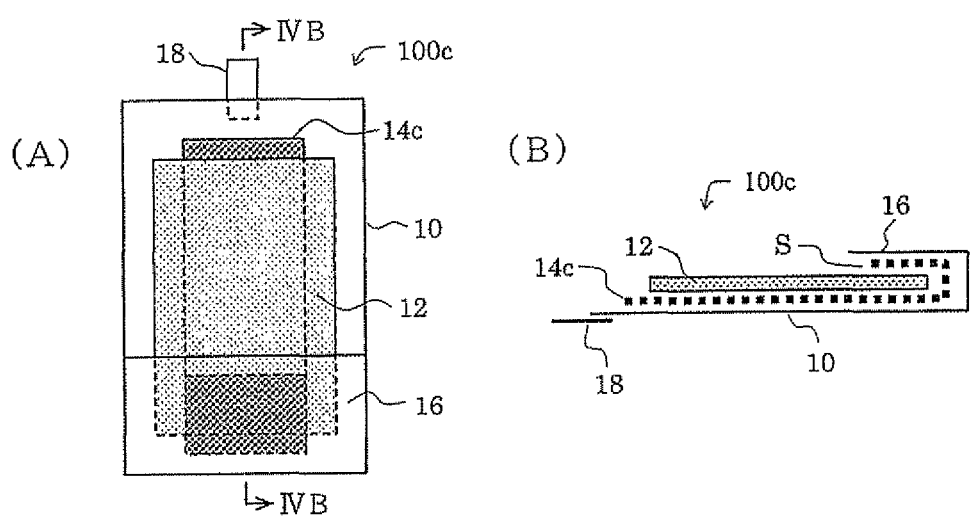
FIGS. 4A and 4B are schematic views illustrating yet another example of the absorbent article according to the present invention.

FIGS. 4A and 4B are schematic views illustrating yet another example of the absorbent article according to the present invention. FIG. 4A is a plan view, and FIG. 4B is a vertical end view taken along the line IVB-IVB of FIG. 4A.

An absorbent article 100c illustrated in FIGS. 4A and 4B is basically the same as the absorbent article 100 except that a back-up sheet 14c is folded back on a rear side with respect to the rear end portion of the absorber 12 so that a rear end portion of the back-up sheet 14c exists on the upper side of the absorber 12. In this mode, a large part of the back-up sheet 14c exists in the internal space S of the liquid-storing portion 16, and the back-up sheet 14c and the liquid-storing portion 16 are in close cooperation with each other. Thus, the above-mentioned leakage preventing effect of the absorbent article 100 is more sufficiently exerted.

Figure 5:
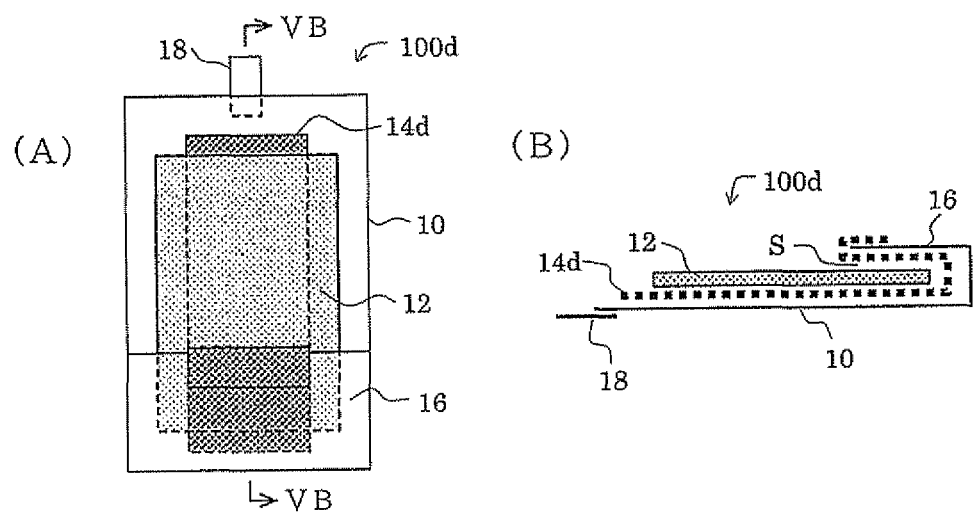
FIGS. 5A and 5B are schematic views illustrating yet another example of the absorbent article according to the present invention.

FIGS. 5A and 5B are schematic views illustrating yet another example of the absorbent article according to the present invention. FIG. 5A is a plan view, and FIG. 5B is a vertical end view taken along the line VB-VB of FIG. 5A.

An absorbent article 100d illustrated in FIGS. 5A and 5B is basically the same as the absorbent article 100c except that a back-up sheet 14d is folded back not only on the rear side with respect to the rear end portion of the absorber 12 but also on the front side with respect to a front end portion of the liquid-storing portion 16 of the individual-wrapping sheet 10 so that a rear end portion of the back-up sheet 14d exists on the upper side of the liquid-storing portion 16. In this mode, in addition to the above-mentioned leakage preventing effect of the absorbent article 100c, urine moving along the skin of the wearer toward the outside of the absorbent article 100d is retained by a part of the back-up sheet 14d, which exists on the upper side of the liquid-storing portion 16. Thus, a spreading-leakage preventing effect is exerted. In particular, when the rear end portion of the back-up sheet 14d is formed in conformity with a cleft of the buttocks of the wearer, the spreading-leakage preventing effect is more sufficiently exerted.

In particular, when the absorbent article according to the present invention is used as an incontinence pad for women, urine is liable to flow along the cleft toward the rear side (back) because of a body shape peculiar to women, and hence it is important to prevent spreading leakage. In addition, although downsizing of the incontinence pad for women has been demanded, it is conventionally difficult for downsized incontinence pads to prevent the spreading leakage of urine toward the rear side. However, the absorbent article 100d includes the back-up sheet 14d, and hence significantly effectively prevents the spreading leakage of urine toward the rear side.

The back-up sheet 14d is held in contact with the absorber 12 mainly in the internal space S of the liquid-storing portion 16. Thus, a capillary phenomenon and the like cause urine retained by the back-up sheet 14d to move along a surface or through an inside of the back-up sheet 14d. Finally, a part of the urine is absorbed by the absorber 12.

As a material for the back-up sheet 14d, it is preferred to use, of the above-mentioned various materials, the cotton gauze, the hydrophilic non-woven fabric, and the spun-lace because urine positively moves owing to a capillary phenomenon.

Figure 6:
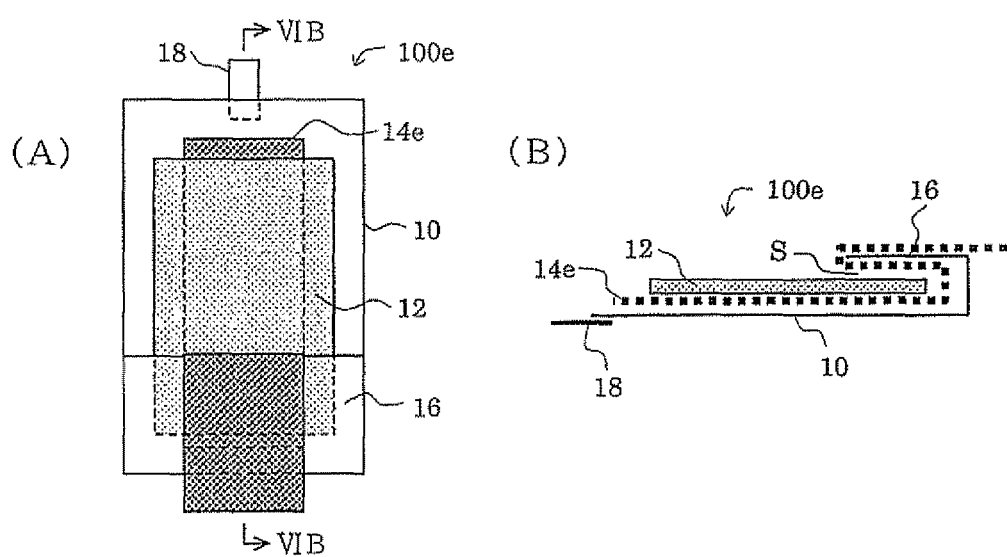
FIGS. 6A and 6B are schematic views illustrating yet another example of the absorbent article according to the present invention.

FIGS. 6A and 6B are schematic views illustrating yet another example of the absorbent article according to the present invention. FIG. 6A is a plan view, and FIG. 6B is a vertical end view taken along the line VIB-VIB of FIG. 6A.

An absorbent article 100e illustrated in FIGS. 6A and 6B is basically the same as the absorbent article 100d except that a rear end portion of a back-up sheet 14e exists on a rear side with respect to the liquid-storing portion 16. In this mode, a large area of the back-up sheet 14e is exposed on the liquid-storing portion 16. Thus, even when leakage occurs, urine can be captured by the exposed part. In particular, when the rear end portion of the back-up sheet 14e is formed in conformity with a cleft of the buttocks of the wearer, the spreading-leakage preventing effect is more sufficiently exerted.

FIGS. 7A to 7D are schematic vertical end views illustrating yet other various examples of the absorbent article according to the present invention.

Figure 7:
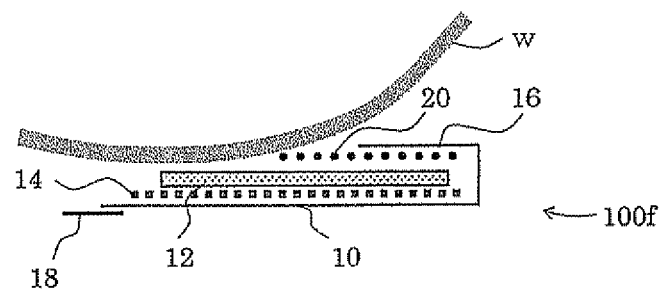
FIGS. 7A to 7D are schematic vertical end views illustrating yet other various examples of the absorbent article according to the present invention.
Figure 7:
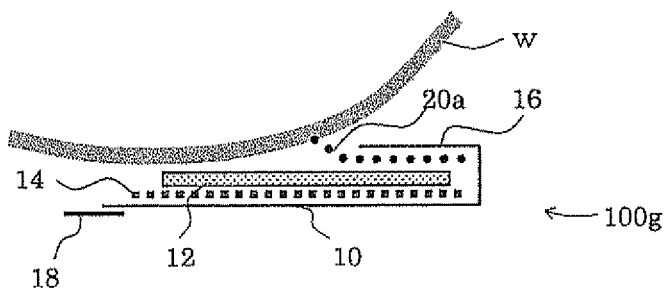
Figure 7:
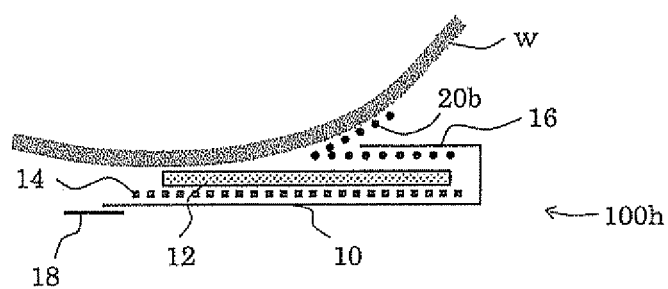
Figure 7:
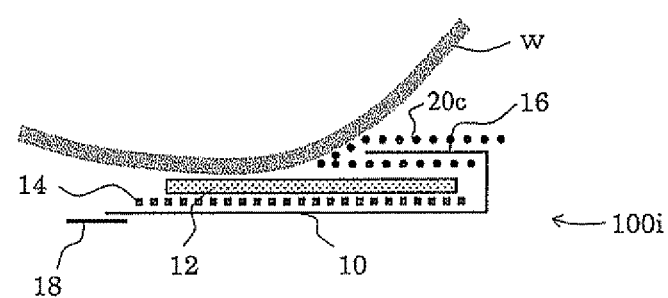

An absorbent article 100f illustrated in FIG. 7A is basically the same as the absorbent article 100 except that a spreading-leakage preventing sheet 20 is further provided on the upper side of the absorber 12.

The material for the spreading-leakage preventing sheet 20 is not particularly limited as long as aqueous liquid can be retained. For example, the same materials as those of the above-mentioned back-up sheet 14 can be used. Of those, it is preferred to use the cotton gauze, the hydrophilic non-woven fabric, and the spun-lace because urine positively moves by a capillary phenomenon. Alternatively, a bundle of slivers, hydrophilized synthetic fiber tow, and hydrophilic sponges having open cells may be used.

A part of the spreading-leakage preventing sheet 20 exists in the internal space S of the liquid-storing portion 16, and another part of the spreading-leakage preventing sheet 20 is exposed out of the internal space S of the liquid-storing portion 16.

The part of the spreading-leakage preventing sheet 20 exposed out of the internal space S of the liquid-storing portion 16 is brought into contact with the skin of a wearer w, and captures urine spreading along the skin of the wearer w. In addition, the spreading-leakage preventing sheet 20 is held in contact with the absorber 12 mainly in the internal space S of the liquid-storing portion 16. Thus, a capillary phenomenon and the like cause urine retained by the spreading-leakage preventing sheet 20 to move along a surface or through an inside of the spreading-leakage preventing sheet 20. Finally, a part of the urine is absorbed by the absorber 12. In this way, the spreading-leakage preventing sheet 20 prevents spreading leakage.

An absorbent article 100g illustrated in FIG. 7B is basically the same as the absorbent article 100f except that a front end part of a spreading-leakage preventing sheet 20a is directed upward. In this mode, in comparison with the case of the spreading-leakage preventing sheet 20, the spreading-leakage preventing sheet 20a and the skin of the wearer w are more reliably brought into contact with each other, and hence the spreading-leakage preventing effect is more sufficiently exerted.

An absorbent article 100h illustrated in FIG. 7C is basically the same as the absorbent article 100f except that a spreading-leakage preventing sheet 20b is folded back on the front side with respect to the front end portion of the liquid-storing portion 16. In this mode, a contact area between the spreading-leakage preventing sheet 20b and the skin of the wearer w is larger than that in the case of the spreading-leakage preventing sheet 20, and the spreading-leakage preventing effect is more sufficiently exerted. In order to improve the spreading-leakage preventing effect, a contact state between the spreading-leakage preventing sheet 20b and the skin of the wearer w is particularly important. When a rear end portion of the spreading-leakage preventing sheet 20b is formed in conformity with a cleft of the buttocks of the wearer, the spreading-leakage preventing effect is more sufficiently exerted.

An absorbent article 100i illustrated in FIG. 7D is basically the same as the absorbent article 100h except that a rear end portion of a spreading-leakage preventing sheet 20c on the upper side of the liquid-storing portion 16 exists on the rear side with respect to the liquid-storing portion 16. In this mode, a large area of the spreading-leakage preventing sheet 20c is exposed above the liquid-storing portion 16. Thus, even when leakage occurs, urine can be captured by the exposed part. In particular, when the rear end portion of the spreading-leakage preventing sheet 20c is formed in conformity with a cleft of the buttocks of the wearer, the spreading-leakage preventing effect is more sufficiently exerted.

A horizontal width of the spreading-leakage preventing sheet is not particularly limited as long as at least a part of the spreading-leakage preventing sheet can exist in the internal space of the liquid-storing portion.

The spreading-leakage preventing sheet may be bonded with an adhesive or the like to an upper surface of the liquid-storing portion. Whether or not bonding is to be performed can be appropriately selected in accordance with a material, shape, size, and the like of the spreading-leakage preventing sheet.

For example, when the spreading-leakage preventing sheet is formed of a narrow and bulky material such as tape-like polyurethane foam having a horizontal width of approximately 20 mm, the spreading-leakage preventing sheet is preferred to be fixed to the upper surface of the liquid-storing portion such that the spreading-leakage preventing sheet is positioned at a center in the horizontal direction of the upper surface of the liquid-storing portion.

Alternatively, when the spreading-leakage preventing sheet is made of a relatively bulky non-woven fabric such as a cotton spun-lace (for example, with a basis weight of 40 g/m$^2$) having a horizontal width of approximately 40 mm, the spreading-leakage preventing sheet in a wet state is liable to come into intimate contact with the skin of the wearer. Thus, through use of such a property, the spreading-leakage preventing sheet follows the motion of the wearer. In terms of this, the spreading-leakage preventing sheet is preferred not to be fixed to the liquid-storing portion.

Still alternatively, when the spreading-leakage preventing sheet is made of a relatively wide and thin non-woven fabric such as a TCF non-woven fabric (for example, with a basis weight of 25 g/m$^2$) having a horizontal width of approximately 50 mm or more, edge portions on both sides of the spreading-leakage preventing sheet are preferred to be fixed to the upper surface of the liquid-storing portion so that a position of the spreading-leakage preventing sheet does not shift.

Figure 8:
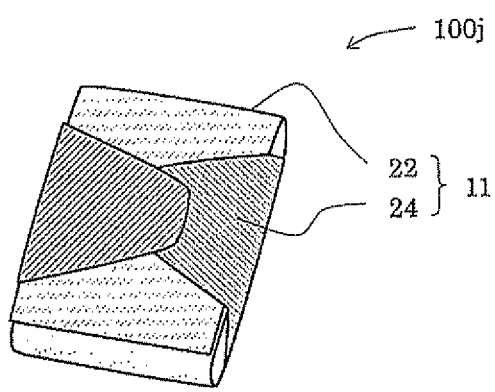
FIGS. 8A and 8B are schematic perspective views illustrating yet another example of the absorbent article according to the present invention.
Figure 8:
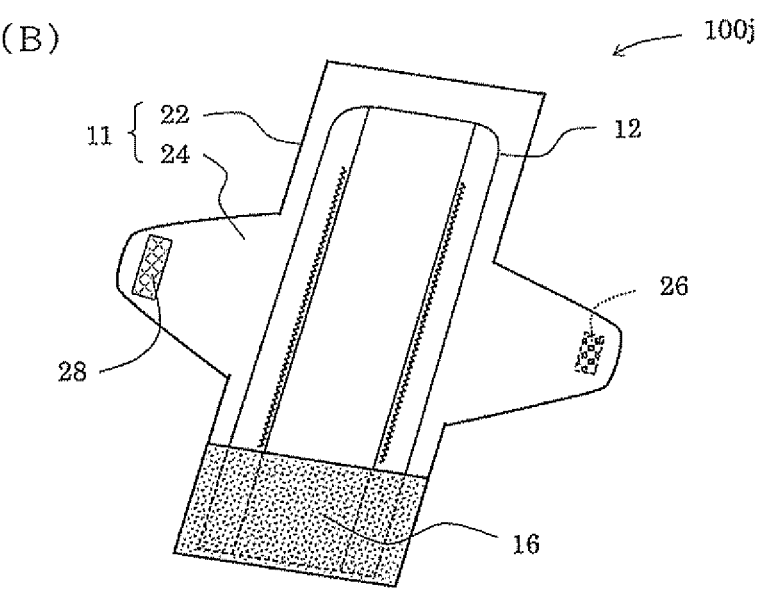

FIGS. 8A and 8B are schematic perspective views illustrating yet another example of the absorbent article according to the present invention. FIG. 8A illustrates a state in which the absorbent article is folded in three, and FIG. 8B illustrates a state in which the absorbent article is unfolded. Note that, in FIGS. 8A and 8B, the back-up sheet is omitted.

An absorbent article 100j illustrated in FIGS. 8A and 8B is basically the same as the absorbent article 100 except that an individual-wrapping sheet 11 includes an individual-wrapping-sheet main-body portion 22 and a pair of wing portions 24 on both left and right sides of the individual-wrapping-sheet main-body portion 22, and the pair of wing portions 24 being coupleable to each other on either an upper side or a lower side of the individual-wrapping-sheet main-body portion 22. Further, the absorbent article 100j does not include a sealing tape.

As illustrated in FIG. 8B, in the absorbent article 100j, a male member 26 is provided on the back surface of a right wing portion 24, and a female member 28 is provided on the upper surface of a left wing portion 24. By folding the left wing portion 24 after folding the right wing portion 24 over the upper side of the individual-wrapping-sheet main-body portion 22, the female member 28 of the left wing portion 24 is placed over the male member 26 of the right wing portion 24 to be in contact therewith. In this way, the left wing portion 24 and the right wing portion 24 are coupled to each other by fitting of the male member 26 and the female member 28.

As illustrated in FIG. 8A, until immediately before use after manufacture, the absorbent article 100j remains folded in three in the front-rear direction on both sides of the pair of wing portions 24. In other words, the pair of wing portions 24 are coupled to each other on the individual-wrapping-sheet main-body portion 22. With this, a sanitary condition of the absorber 12 and other members existing inside the individual-wrapping-sheet main-body portion 22 is satisfactorily maintained. In this way, even without a sealing tape, the sanitary condition can be satisfactorily maintained with the pair of wing portions 24.

Immediately before use, when the individual-wrapping-sheet main-body portion 22 folded in three is unfolded by decoupling the pair of wing portions 24 from each other, the followings appear: a central portion at which the wing portions 24 were coupled; a rear portion including the liquid-storing portion 16; and a front portion at which the absorber 12 is exposed (refer to FIG. 8B).

At the time of use, as in a case of wearing a general sanitary napkin, the absorbent article 100j is arranged on an inner side of an underwear garment. Then, by folding the right wing portion after folding the left wing portion 24 beneath the individual-wrapping-sheet main-body portion 22 so as to wrap a crotch portion of the underwear garment, the female member 28 of the left wing portion 24 and the male member 26 of the right wing portion 24 are fitted to each other so that the left wing portion 24 and the right wing portion 24 are coupled to each other. In this way, the underwear garment and the absorbent article 100j can be kept from shifting with respect to each other.

After use, the absorbent article 100j is detached from the underwear garment, and then, as illustrated in FIG. 8A, is folded in three in the front-rear direction on the front and rear sides of the pair of wing portions 24. With this, the absorbent article 100j can be disposed of so that urine is not exposed to the outside.

In one of the preferred modes of the present invention, as in the case of the absorbent article 100j, the individual-wrapping sheet includes the individual-wrapping-sheet main-body portion and the pair of wing portions on both the left and right sides of the individual-wrapping-sheet main-body portion, the pair of wing portions being coupleable to each other on either the upper side or the lower side of the individual-wrapping-sheet main-body portion.

The mode in which the pair of wing portions can be coupled to each other is not particularly limited. For example, the pair of wing portions may be coupled to each other by tackifiers applied thereto. Further, as in the case of the absorbent article 100j, one of the pair of wing portions may be provided with the male member and another of the pair of wing portions may be provided with the female member so that the pair of wing portions are coupled to each other by fitting of the male member and the female member.

Figure 9:
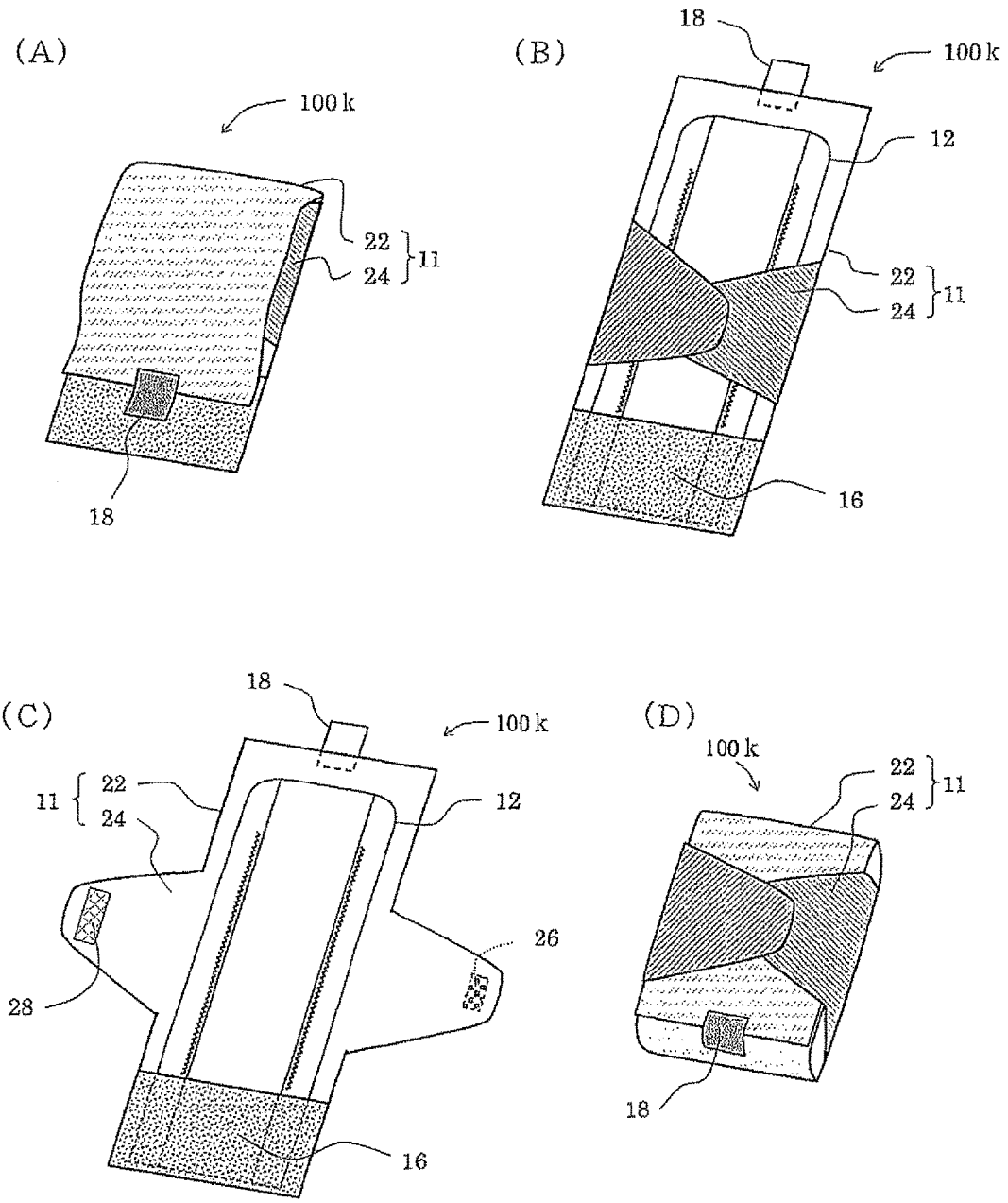
FIGS. 9A to 9D are schematic perspective views illustrating yet another example of the absorbent article according to the present invention.

FIGS. 9A to 9D are schematic perspective views illustrating yet another example of the absorbent article according to the present invention. FIG. 9A illustrates a state in which the absorbent article is folded in two before use. FIGS. 9B and 9C each illustrate a state in which the absorbent article is unfolded immediately before use. FIG. 9D illustrates a state in which the absorbent article is folded in three after use. Note that, in FIGS. 9A to 9D, the back-up sheet is omitted.

An absorbent article 100k illustrated in FIGS. 9A to 9D is basically the same as the absorbent article 100j except that the sealing tape 18 is provided as in the case of the absorbent article 100.

As illustrated in FIG. 9A, until immediately before use after manufacture, the absorbent article 100k remains folded in two in the front-rear direction on the front side of the pair of wing portions 24, and the sealing tape 18 is adhered to the liquid-storing portion 16 of the individual-wrapping sheet 11. With this, a sanitary condition of the absorber 12 and other members existing inside of the individual-wrapping-sheet main-body portion 22 is satisfactorily maintained.

Immediately before use, by peeling the sealing tape 18 off the liquid-storing portion 16 of the individual-wrapping sheet 11, the individual-wrapping-sheet main-body portion 22 folded in two is unfolded (refer to FIG. 9B). Then, by decoupling the pair of wing portions 24 from each other, the individual-wrapping-sheet main-body portion 22 folded in two is further unfolded (refer to FIG. 9C).

At the time of use, the absorbent article 100k is arranged on an inner side of an underwear garment. Then, by folding the right wing portion 24 after folding the left wing portion 24 beneath the individual-wrapping-sheet main-body portion 22 so as to wrap a crotch portion of the underwear garment, the female member 28 of the left wing portion 24 and the male member 26 of the right wing portion 24 fitted to each other so that the left wing portion 24 and the right wing portion 24 are coupled to each other. In this way, the underwear garment and the absorbent article 100k can be kept from shifting with respect to each other.

After use, the absorbent article 100k is detached from the underwear garment, and then, as illustrated in FIG. 9D, is folded in three in the front-rear direction on the front and rear sides of the pair of wing portions 24. Further, the sealing tape 18 is adhered to the liquid-storing portion 16 of the individual-wrapping sheet 11, and the pair of wing portions 24 are coupled to each other on the upper side of the individual-wrapping-sheet main-body portion 22 folded in three. With this, the absorbent article look can be disposed of so that urine remains untouched. Further, the three-folded state is maintained by coupling at two points, and hence, even when the absorbent article 100k is roughly handled at the time of disposal, the three-folded state is more easily maintained than that in the case of the absorbent article 100j.

In the following, detailed description is made of various modes of the individual-wrapping sheet to be used in the absorbent article according to the present invention.

Figure 10:
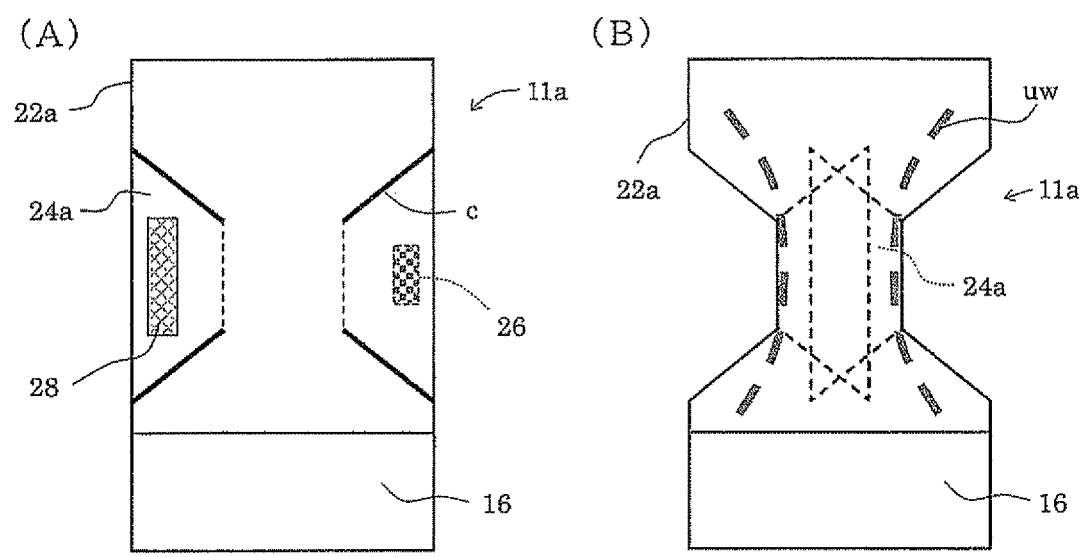
FIGS. 10A and 10B are schematic plan views illustrating an example of an individual-wrapping sheet.

FIGS. 10A and 10B are schematic plan views illustrating an example of the individual-wrapping sheet. FIG. 10A illustrates a state in which a pair of wing portions are unfolded, and FIG. 10B illustrates a state in which the pair of wing portions are folded.

An individual-wrapping-sheet main-body portion 22a and a pair of wing portions 24a of an individual-wrapping sheet 11a illustrated FIGS. 10A and 10B are formed by making four cutouts c on an individual-wrapping sheet material having a rectangular shape. As described above, the individual-wrapping sheet 11a is formed by making the four cutouts c on the individual-wrapping sheet material having the rectangular shape, and hence waste parts not to be used as the individual-wrapping sheet are not formed at the time of manufacture.

Until immediately before use after manufacture, the pair of wing portions 24a of the individual-wrapping sheet 11a remain folded inward along dotted lines of FIG. 10A. At the time of use, as illustrated in FIG. 10B, the pair of wing portions 24a are folded to the opposite side and coupled to each other so as to wrap a crotch portion of an underwear garment uw.

Figure 11:
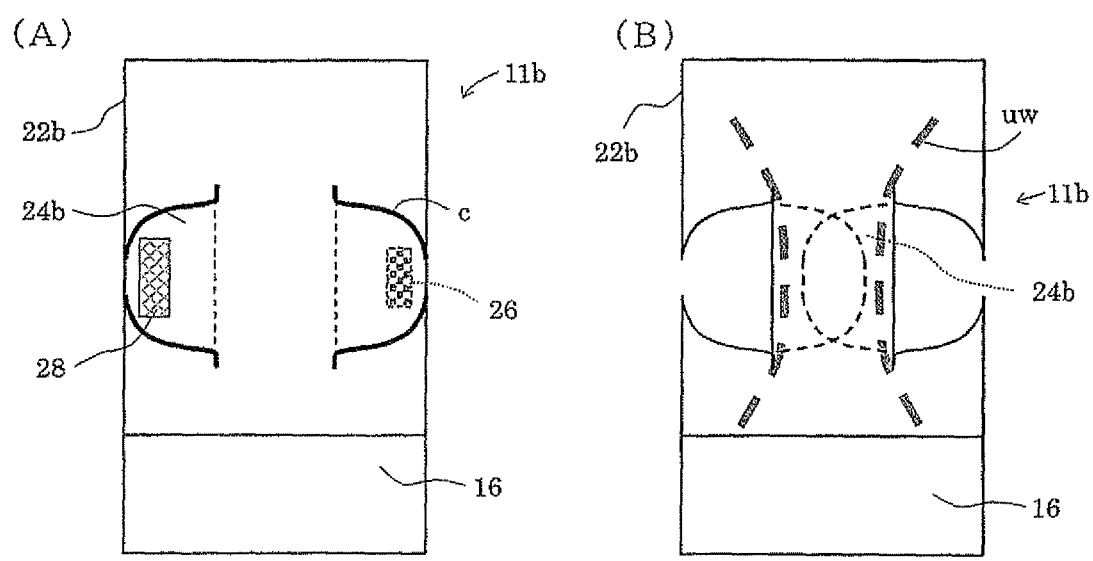
FIGS. 11A and 11B are schematic plan views illustrating another example of the individual-wrapping sheet.

FIGS. 11A and 11B are schematic plan views illustrating another example of the individual-wrapping sheet. FIG. 11A illustrates a state in which a pair of wing portions are unfolded, and FIG. 11B illustrates a state in which the pair of wing portions are folded.

An individual-wrapping sheet 11b illustrated in FIGS. 11A and 11B is basically the same as the individual-wrapping sheet 11a except that an individual-wrapping-sheet main-body portion 22b and a pair of wing portions 24b are formed in different shapes owing to a difference in shape of the cutouts c.

Until immediately before use after manufacture, the pair of wing portions 24b of the individual-wrapping sheet 11b remain folded inward along dotted lines of FIG. 11A. At the time of use, as illustrated in FIG. 11B, the pair of wing portions 24b are folded to the opposite side and coupled to each other so as to wrap the crotch portion of the underwear garment uw.

Figure 12:
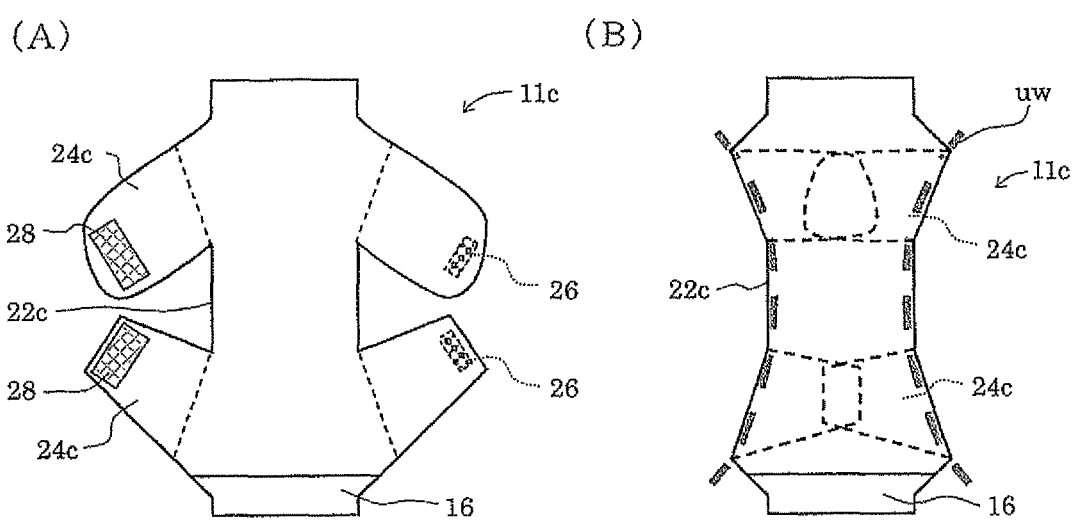
FIGS. 12A and 12B are schematic plan views illustrating still another example of the individual-wrapping sheet.

FIGS. 12A and 12B are schematic plan views illustrating still another example of the individual-wrapping sheet. FIG. 12A illustrates a state in which two pairs of wing portions are unfolded, and FIG. 12B illustrates a state in which the two pairs of wing portions are folded.

An individual-wrapping sheet 11c illustrated in FIGS. 12A and 12B includes an individual-wrapping-sheet main-body portion 22c and two pairs of wing portions 24c provided on the front and rear on both sides of the individual-wrapping-sheet main-body portion 22c.

Until immediately before use after manufacture, the two pairs of wing portions 24c of the individual-wrapping sheet 11c remain folded inward along dotted lines of FIG. 12A. At the time of use, as illustrated in FIG. 12B, the two pairs of wing portions 24c are folded to the opposite side and coupled respectively to each other so as to wrap the crotch portion of the underwear garment uw. As described above, the individual-wrapping-sheet main-body portion 22c includes the two pairs of wing portions 24c, and hence it is possible to more effectively keep the individual-wrapping-sheet main-body portion 22c and the underwear garment uw from shifting with respect to each other.

Further, the individual-wrapping-sheet main-body portion 22c of the individual-wrapping sheet 11c is shaped so as to be widened from a central portion toward the front side and the rear side. With this, the individual-wrapping-sheet main-body portion 22c is more likely to conform to a shape of the crotch portion of the underwear garment uw. In this manner, the shift with respect to the underwear garment uw can be more effectively prevented.

After use, of the two pairs of wing portions 24c, one pair on the front side are folded inward, and then the 22c is folded in two. Thereafter, another pair on the rear side are coupled to each other over the two-folded individual-wrapping-sheet main-body portion 22c. In this state, the individual-wrapping sheet 11c can be disposed of.

Figure 13:
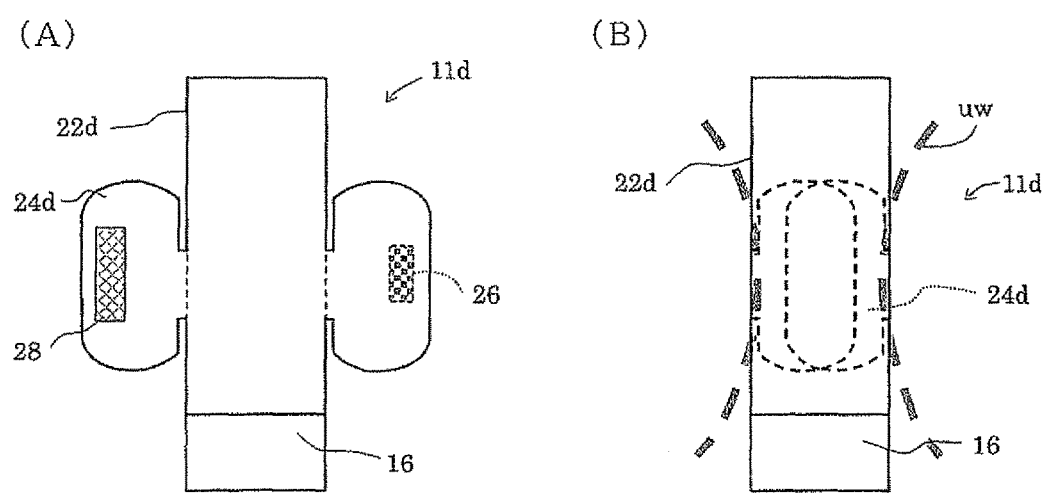
FIGS. 13A and 13B are schematic plan views illustrating yet another example of the individual-wrapping sheet.

FIGS. 13A and 13B are schematic plan views illustrating yet another example of the individual-wrapping sheet. FIG. 13A illustrates a state in which a pair of wing portions are unfolded, and FIG. 13B illustrates a state in which the pair of wing portions are folded.

An individual-wrapping sheet 11d illustrated in FIGS. 13A and 13B includes an individual-wrapping-sheet main-body portion 22d and a pair of wing portions 24d.

Until immediately before use after manufacture, the pair of wing portions 24d of the individual-wrapping sheet 11d remain folded inward along dotted lines of FIG. 13A. At the time of use, as illustrated in FIG. 13B, the pair of wing portions 24d are folded to the opposite side and coupled to each other so as to wrap the crotch portion of the underwear garment uw.

The individual-wrapping sheet 11d has such a shape that slits are provided on the front and rear of coupling portions between the individual-wrapping-sheet main-body portion 22d and each of the pair of wing portions 24d. With this, edge portions of the crotch portion of the underwear garment uw are more likely to enter into the slits between the individual-wrapping-sheet main-body portion 22d and the pair of wing portions 24d. In this manner, the shift with respect to the underwear garment uw can be more effectively prevented. When the slit-forming parts are reinforced with a material which suppresses slipping with respect to the underwear garment uw (reinforcement by attachment, application, or the like of, for example, synthetic rubber), the shift is further more effectively prevented.

Figure 14:
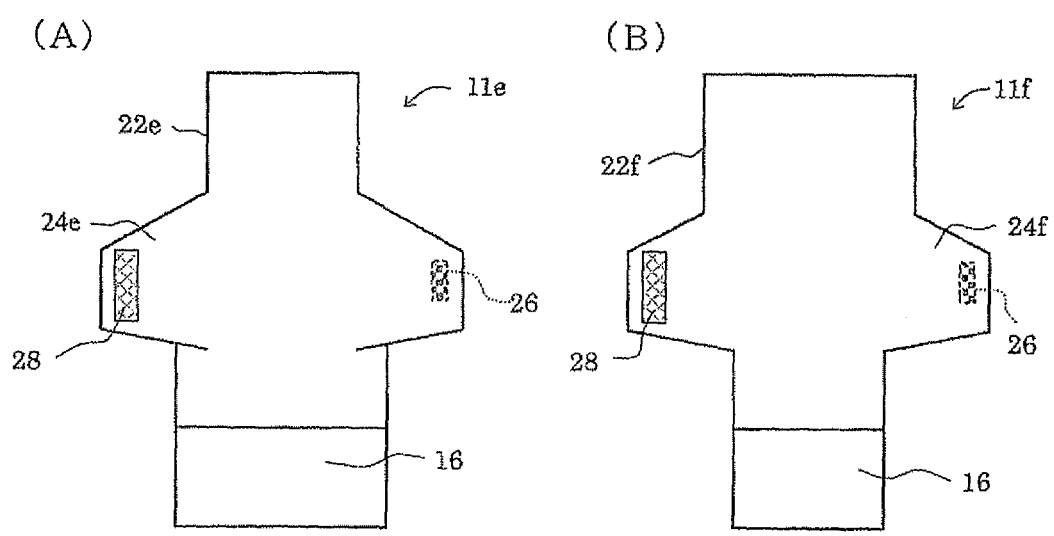
FIGS. 14A and 14B are schematic plan views illustrating yet other various examples of the individual-wrapping sheet.

FIGS. 14A and 14B are schematic plan views illustrating yet other various examples of the individual-wrapping sheet.

An individual-wrapping sheet 11e illustrated in FIG. 14A includes an individual-wrapping-sheet main-body portion 22e and a pair of wing portions 24e, individual-wrapping-sheet main-body portion 22e having a horizontal width larger on the rear from the pair of wing portions 24e than on the front therefrom. In this mode, the width of the liquid-storing portion 16 is large, and hence there is an advantage that an internal space to be formed of the liquid-storing portion 16 becomes larger. Further, owing to the large width of the liquid-storing portion 16, the liquid-storing portion 16 may be designed to have a short front-rear length.

An individual-wrapping sheet 11f illustrated in FIG. 14B includes an individual-wrapping-sheet main-body portion 22f and a pair of wing portions 24f, the individual-wrapping-sheet main-body portion 22f having a horizontal width smaller on the rear from the pair of wing portions 24f than on the front therefrom. In this mode, a horizontal width of a back-up sheet (not shown) to be arranged on the upper side of the individual-wrapping sheet 11f is set to be large so that a large amount of urine can be temporarily absorbed. With this, the liquid-storing portion 16 can be further compactified.

Figure 15:
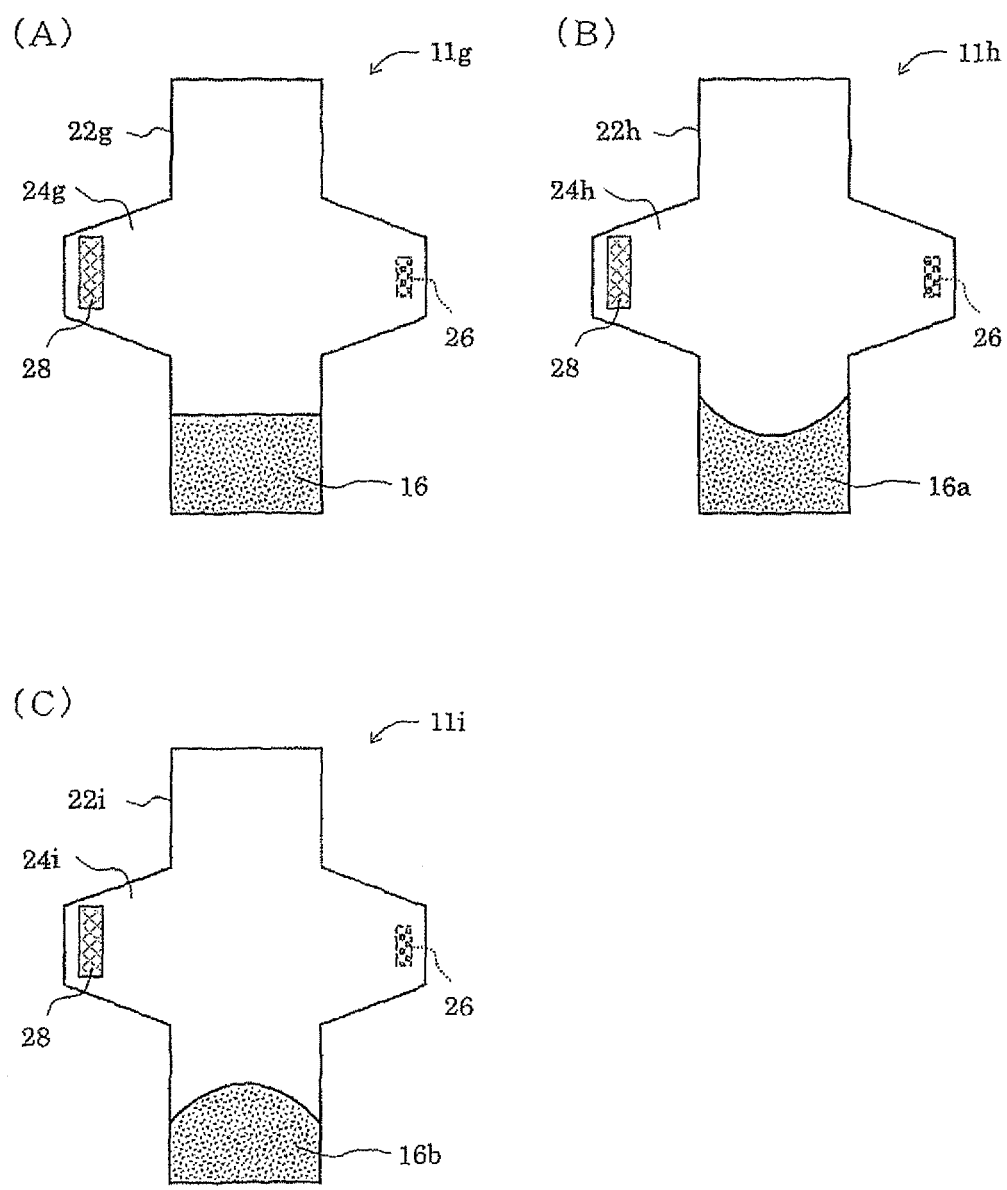
FIGS. 15A to 15C are schematic plan views illustrating yet other various examples of the individual-wrapping sheet.

FIGS. 15A to 15C are schematic plan views illustrating yet other various examples of the individual-wrapping sheet.

An individual-wrapping sheet 11g illustrated in FIG. 15A includes an individual-wrapping-sheet main-body portion 22g and a pair of wing portions 24g, and the front end of the liquid-storing portion 16 has a horizontally linear shape.

An individual-wrapping sheet 11h illustrated in FIG. 15B includes an individual-wrapping-sheet main-body portion 22h and a pair of wing portions 24h, and a front end of a liquid-storing portion 16a is shaped such that the liquid-storing portion 16a is short at a central portion in the horizontal direction and become longer toward both left and right sides. In this mode, an exposed area of an absorber (not shown) at the central portion is larger than that in the mode of the individual-wrapping sheet 11g illustrated in FIG. 15A.

An individual-wrapping sheet 11i illustrated in FIG. 15C includes an individual-wrapping-sheet main-body portion 22i and a pair of wing portions 24l, and a front end portion of a liquid-storing portion 16b is shaped such that the liquid-storing portion 16b is longer at a central portion in the horizontal direction and become smaller toward both the left and right sides. In this mode, the exposed area of the absorber (not shown) at the central portion is smaller than that in the mode of the individual-wrapping sheet 11g illustrated in FIG. 15A. Thus, urine is less liable to leak rearward.

Figure 16:
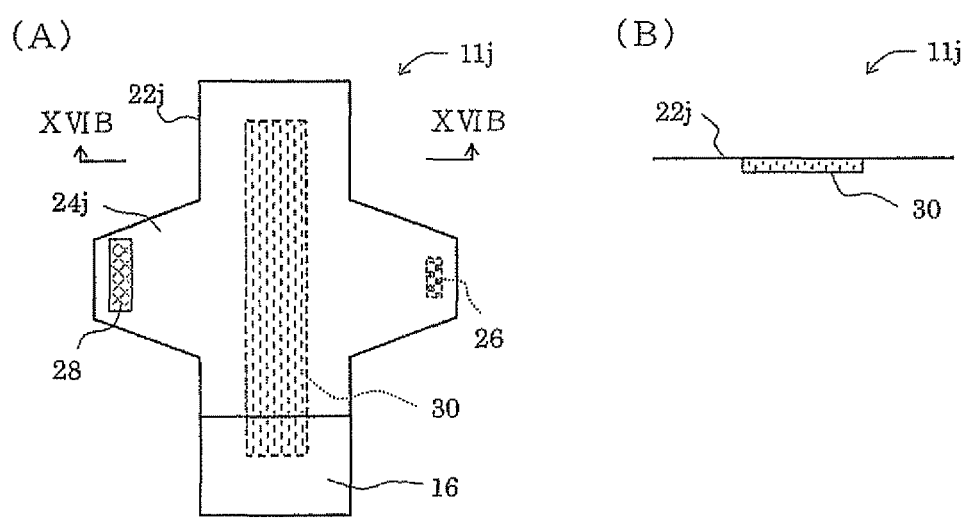
FIGS. 16A and 16B are schematic views illustrating yet another example of the individual-wrapping sheet.

FIGS. 16A and 16B are schematic views illustrating yet another example of the individual-wrapping sheet. FIG. 16A is a plan view, and FIG. 16B is a lateral end view taken along the line XVIB-XVIB of FIG. 16A.

An individual-wrapping sheet 11j illustrated in FIGS. 16A and 16B includes an individual-wrapping-sheet main-body portion 22j and a pair of wing portions 24j, and further includes, on a lower-side surface thereof, a tackifier 30 adherable to an inner surface of an underwear garment of a wearer at the time of wearing. In this manner, the shift with respect to the underwear garment uw can be more effectively prevented.

A type of the tackifier 30 is not particularly limited as long as the tackifier can adhere to the inner surface of the underwear garment of the wearer at the time of wearing.

The tackifier 30 exists over substantially the entire length in the front-rear direction of the lower-side surface of the individual-wrapping-sheet main-body portion 22j, but the present invention is not limited thereto. For example, the tackifier 30 may exist only at a front-side part, at a rear-side part, or at a plurality of points (for example, arranged on both the left and right sides (two points) so as to extend in the front-rear direction).

Figure 17:
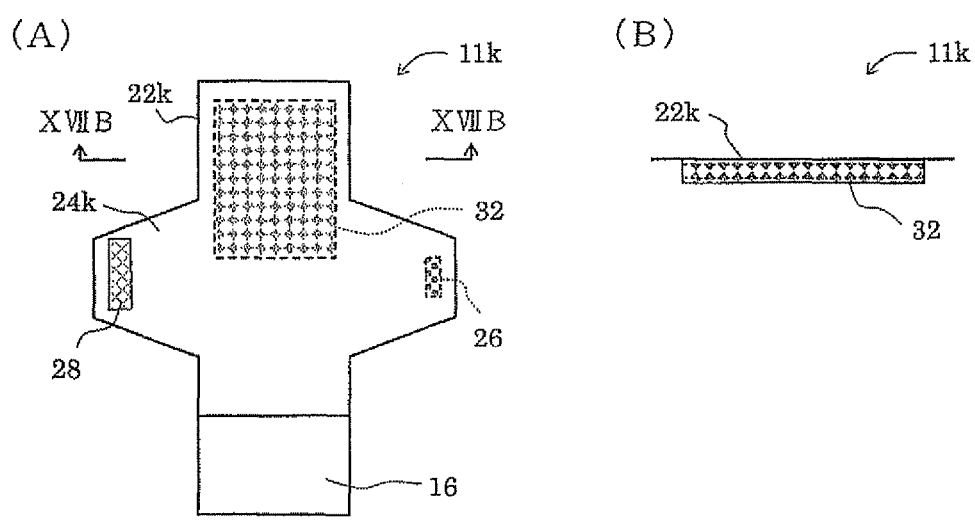
FIGS. 17A and 17B are schematic views illustrating yet another example of the individual-wrapping sheet.

FIGS. 17A and 17B are schematic views illustrating yet another example of the individual-wrapping sheet. FIG. 17A is a plan view, and FIG. 17B is a lateral end view taken along the line XVIIB-XVIIB of FIG. 17A.

An individual-wrapping sheet 11k illustrated in FIGS. 17A and 17B includes an individual-wrapping-sheet main-body portion 22k and a pair of wing portions 24k, and further includes, on a lower-side surface thereof, an anti-slip member 32 which suppresses slipping with respect to the inner surface of the underwear garment of the wearer at the time of wearing. In this manner, the shift with respect to the underwear garment uw can be more effectively prevented.

A material for the anti-slip member 32 is not particularly limited as long as the material suppresses slipping with respect to the inner surface of the underwear garment of the wearer at the time of wearing. For example, urethane foam can be exemplified.

Figure 18:
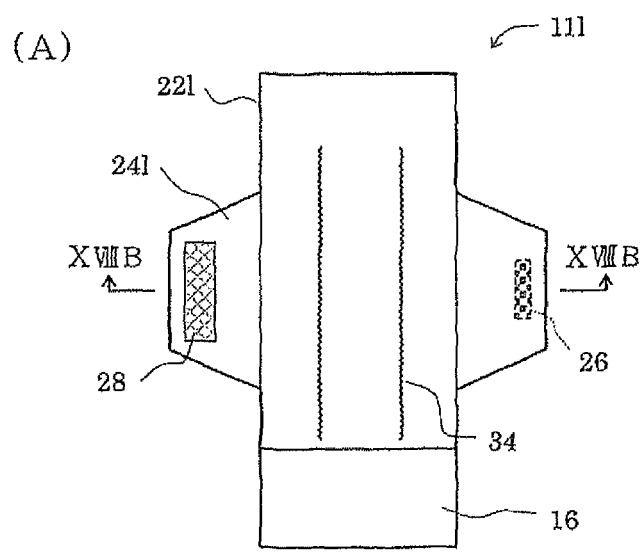
FIGS. 18A and 18B are schematic views illustrating yet another example of the individual-wrapping sheet.
Figure 18:
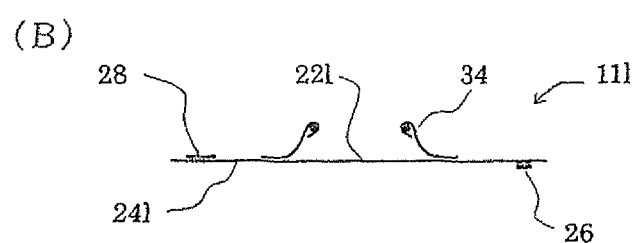

In FIGS. 17A and 18B, the anti-slip member 32 exists only at a front-side part of the lower-side surface of the individual-wrapping-sheet main-body portion 22k, but the present invention is not limited thereto. For example, the anti-slip member 32 may exist over substantially the entire length in the front-rear direction, only at a rear-side part, or at a plurality of points (for example, arranged on both the left and right sides (two points) so as to extend in the front-rear direction).

FIGS. 18A and 18B are schematic views illustrating yet another example of the individual-wrapping sheet. FIG. 18A is a plan view, and FIG. 18B is a lateral end view taken along the line XVIIIB-XVIIIB of FIG. 18A.

An individual-wrapping sheet ill illustrated in FIGS. 18A and 18B includes an individual-wrapping-sheet main-body portion 22l and a pair of wing portions 24l, and further includes, on an upper-side surface thereof, a pair of side-barrier portions 34 standing upward, the pair of side-barrier portions 34 being provided on both the left and right sides.

Each of the side-barrier portions 34 is a gather-like stretchable member formed by inserting a rubber band inside a non-woven fabric, and extends in the front-rear direction on both the left and right sides on the upper-side surface of the individual-wrapping-sheet main-body portion 22l of the individual-wrapping sheet ill.

In the present invention, a shape, a structure, and the like of the side-barrier portion are not limited to those in this mode. For example, a shape, a structure, and the like which are the same as those of a conventional inner gather and a conventional outer gather can be employed.

Further, in FIG. 18A, the side-barrier portions 34 do not extend up to a front end or a rear end of the individual-wrapping sheet 11l, but in the present invention, the side-barrier portions may extend up to the front end and/or the rear end of the individual-wrapping sheet.

The side-barrier portions 34 are capable of preventing the movement of urine to the horizontal direction, which may cause spreading leakage.

Figure 19:
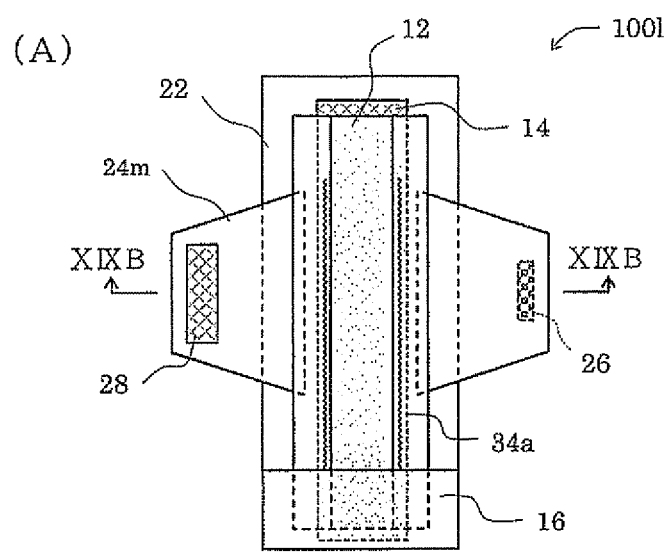
FIGS. 19A and 19B are schematic views illustrating yet another example of the absorbent article according to the present invention.
Figure 19:
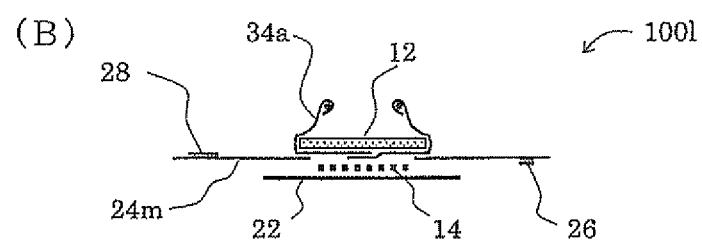

FIGS. 19A and 19B are schematic views illustrating yet another example of the absorbent article according to the present invention. FIG. 19A is a plan view, and FIG. 19B is a lateral end view taken along the line XIXB-XIXB of FIG. 19A.

An absorbent article 100l illustrated in FIGS. 19A and 19B is basically the same as the absorbent article 100 except the following points: a lower side of the absorber 12 is covered with a hydrophobic non-woven fabric; a pair of side-barrier portions 34a are provided, which are formed by causing the hydrophobic non-woven fabric to stand upward on both the left and right sides of the absorber 12; and a pair of wing portions 24m are formed on both the left and right sides of the hydrophobic non-woven fabric. In this mode, the wing portions and the side-barrier portions are integrated with the absorber, and hence a shape of the individual-wrapping sheet can be markedly simplified (for example, a rectangular shape as that of the individual-wrapping-sheet main-body portion 22).

As described above, the absorbent article of the present invention has been described in detail based on the embodiment modes illustrated in the drawings. However, the present invention is not limited thereto, and structures of the respective members may be replaced by arbitrary structures which may exhibit similar functions.

The structures of the respective members of the embodiment modes may be combined arbitrarily to make other embodiment modes.

The absorbent article of the present invention may suitably be used as an absorbent article for an adult male, an adult female, or a child. Particularly, the absorbent article of the present invention may suitably be used for an incontinence pad for women and a sanitary napkin.

EXAMPLE

In the following, detailed description is made of the present invention by way of examples. Note that, the present invention is not limited to those examples.

Figure 20:
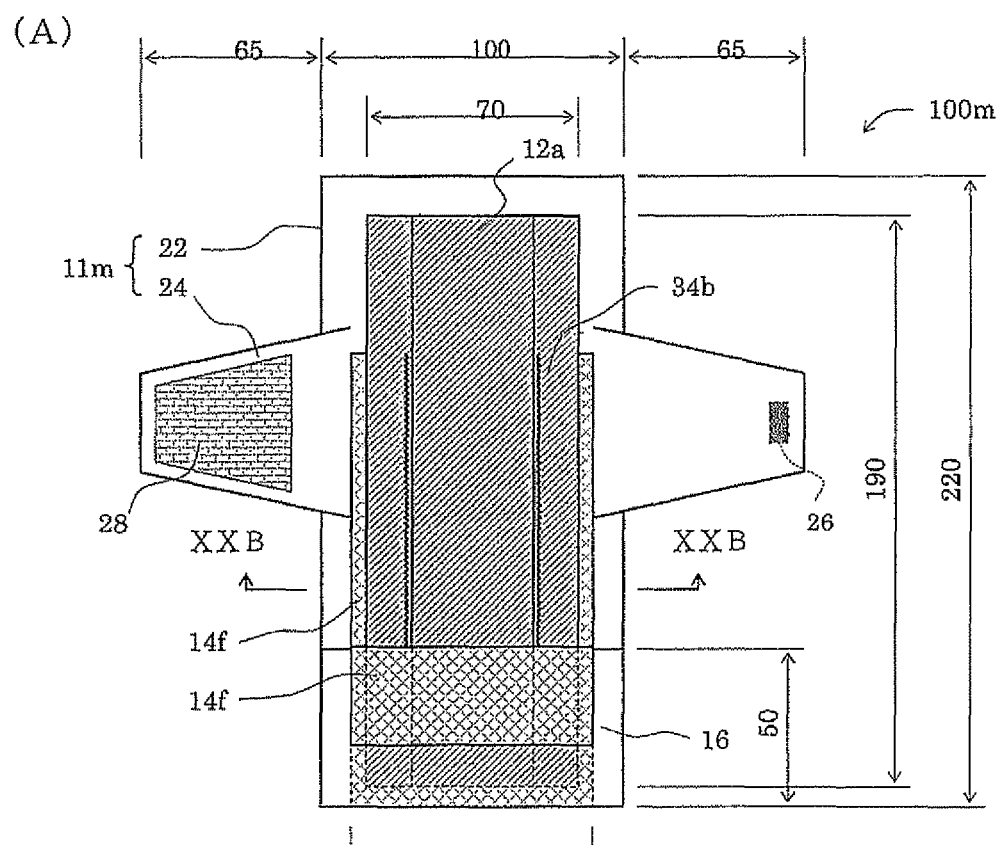
FIGS. 20A and 20B are schematic views illustrating an absorbent article according to an example of the present invention.
Figure 20:
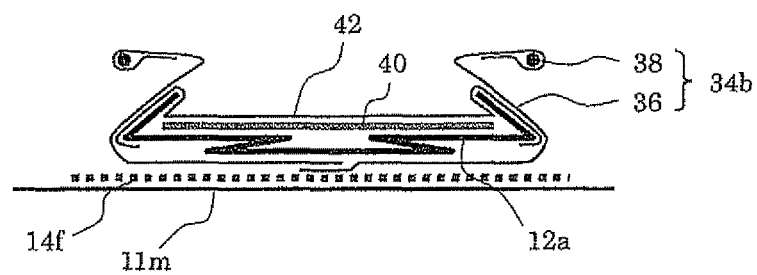

FIGS. 20A and 20B are schematic views illustrating the absorbent article according to an example of the present invention. FIG. 20A is a plan view, and FIG. 20B is a lateral end view taken along the line XXB-XXB of FIG. 20A.

An absorbent article 100m illustrated in FIGS. 20A and 20B is basically the same as the absorbent article 100j except the following points: a back-up sheet 14f is folded back on a rear side with respect to a rear end portion of an absorber 12a and further on a front side with respect to a front end portion of the liquid-storing portion 16 of an individual-wrapping sheet 11m so that a rear end portion of the back-up sheet 14f exists on the upper side of the liquid-storing portion 16; a lower side of the absorber 12a is covered with a side-sheet member 36; a pair of side-barrier portions 34b are provided, which are formed by causing the side-sheet member 36 to stand upward on both the left and right sides of the absorber 12a; both left and right edge portions 38 of the side-sheet member 36 are further folded outward at the side-barrier portions 34b; the absorber 12a is folded at a central portion as illustrated in FIG. 20B and stands upward on both the left and right sides; an acquisition layer 40 is arranged on the upper side of the absorber 12a; and a top sheet 42 is further arranged on the upper side of the acquisition layer 40, the top sheet 42 covering the absorber 12a over both the standing left and right edge portions.

In the side-barrier portions 34b, both the horizontal edge portions 38 of the side-sheet member 36 are further folded outward, and hence an opening width between the side-barrier portions 34b can be increased.

The absorber 12a is folded at the central portion as illustrated in FIG. 20B. Thus, absorbing capability of the absorber can be enhanced, and penetration of absorbed urine to the front-rear direction is further promoted. Further, the absorber 12a stands upward on both the left and right sides, and hence urine is kept from flowing out to both the left and right edge portions. In addition, the absorber 12a supports the side-barrier portions 34b during wearing, and hence the side-barrier portions 34b is prevented from being flattened, with the result that leakage from both the left and right sides is less liable to occur.

The acquisition layer 40 is arranged on the upper side of the absorber 12a, and further, the top sheet 42 is arranged on the upper side thereof. Therefore, absorption and penetration of discharged urine are further stabilized, and excellent wearing comfort is provided to a wearer.

The individual-wrapping sheet 11m is formed of a laminated body of a non-woven fabric and a moisture-permeable PE film (with a basis weight of 37 g/m$^2$, manufactured by Daika Kogyo Co., Ltd.).

The absorber 12a is formed of an SAP sheet (with a basis weight of 200 g/m$^2$, MEGATHIN (trade name) manufactured by Japan Absorbent Technology Institute).

The back-up sheet 14f is made of a TCF non-woven fabric (with a basis weight of 20 g/m$^2$, manufactured by FUTAMURA CHEMICAL CO., LTD.).

Each of the male member 26 and the female member 28 is formed of a mechanical coupling member (manufactured by 3M).

The side-sheet member 36 of the side-barrier portion 34b is made of an SMS non-woven fabric (with a basis weight of 15 g/m$^2$, manufactured by Avgol Ltd.).

Both the horizontal edge portions 38 of the side-barrier portions 34b are made of an elastic material with an elongation percentage of 170% (LYCRA® having a Dtex of 620, manufactured by DU PONT-TORAY CO., LTD.).

The acquisition layer 40 is made of a bulky air-through non-woven fabric (with a basis weight of 40 g/m$^2$, manufactured by KURARAY CO., LTD.).

The top sheet 42 is made of an air-through non-woven fabric (with a basis weight of 20 g/m$^2$, manufactured by KURARAY CO., LTD.).

Further, numerical values in FIGS. 20A and 20B represent dimensions, and are to be read in "mm" units. Note that, the present invention is not limited to those sizes.

Figure 21:
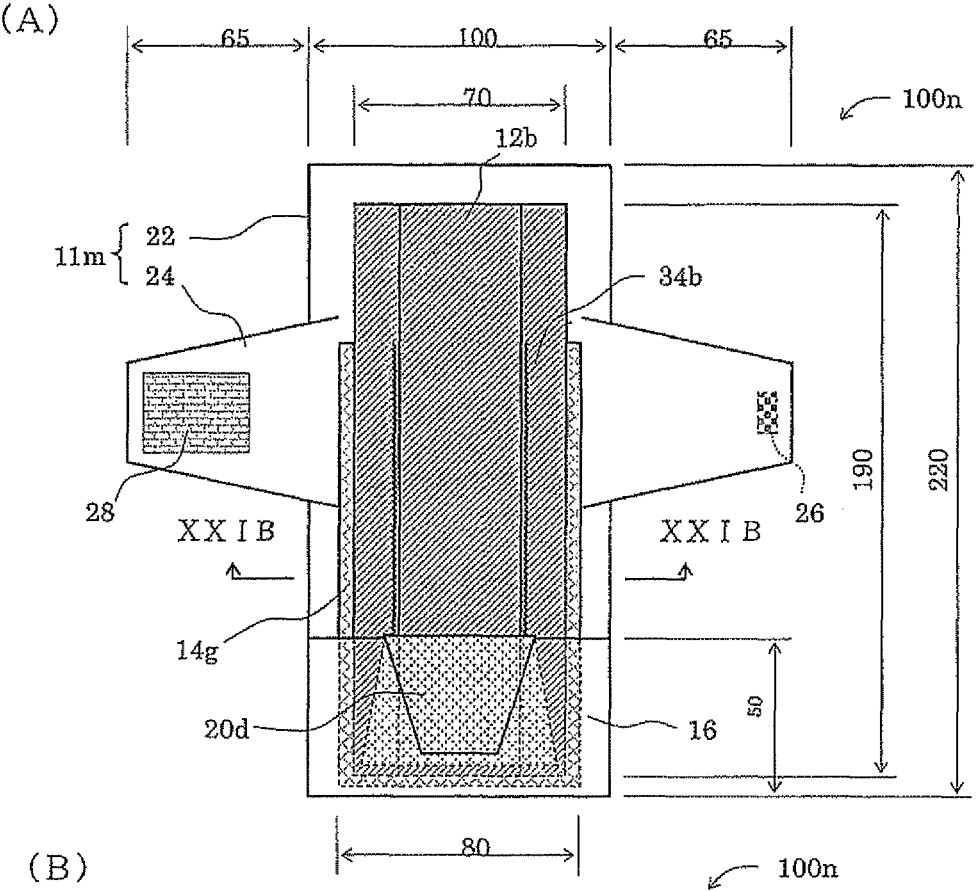
FIGS. 21A and 21B are schematic views illustrating an absorbent article according to another example of the present invention.
Figure 21:
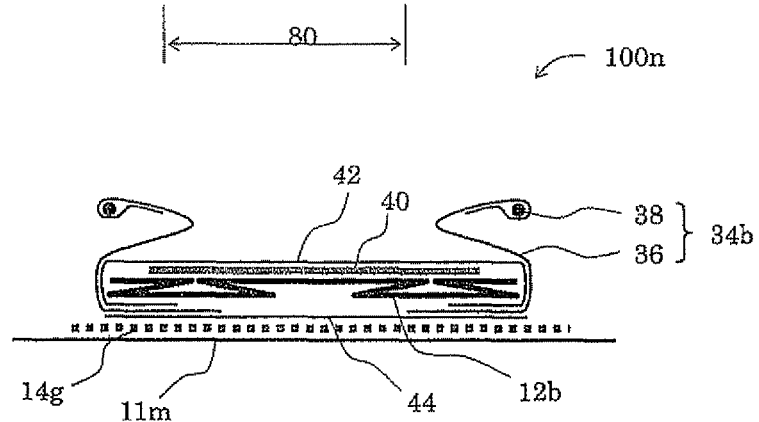

FIGS. 21A and 21B are schematic views illustrating the absorbent article according to another example of the present invention. FIG. 21A is a plan view, and FIG. 21B is a lateral end view taken along the line XXIB-XXIB of FIG. 21A.

An absorbent article 100n illustrated in FIGS. 21A and 21B is basically the same as the absorbent article 100m except the following points: a back-up sheet 14g is not folded back, for example, on a rear side with respect to a rear end portion of an absorber 12b; the absorbent article 100n includes a spreading-leakage preventing sheet 20d folded on a front side with respect to a front end portion of the liquid-storing portion 16; the absorber 12b is folded on both the left and right sides as illustrated in FIG. 21B; the absorber 12b does not stand upward on both the left and right sides; and a liquid-impermeable back sheet 44 is provided under the absorber 12b and on the upper side of the back-up sheet 14g.

The absorber 12b is folded on both the left and right sides as illustrated in FIG. 21B. Thus, absorbing capability of the absorber can be enhanced, and urine flowing in the horizontal direction can be diffused in the front-rear direction.

Each of the back-up sheet 14g and the spreading-leakage preventing sheet 20d has the same function as that of the back-up sheet 14f.

The back sheet 44 is provided, and hence a double leak preventer is formed together with the individual-wrapping sheet 11m. As a result, leakage is less liable to occur.

Note that, the same effect as that described above can be obtained also by using, instead of the back sheet 44, a highly air-permeable and water-resistant barrier sheet having a buffering effect, which is described in WO 02/090106.

The individual-wrapping sheet 11, the absorber 12b, the back-up sheet 14g, the male member 26, the female member 28, the side-sheet members 36 of the side-barrier portions 34b, both the left and right edge portions 38 of the side-barrier portions 34b, the acquisition layer 40, and the top sheet 42 are made of the same materials as those in the case of the absorbent article 100m.

The spreading-leakage preventing sheet 20d is made of a cotton spun-lace non-woven fabric (with a basis weight of 45 g/m$^2$, manufactured by UNITIKA Ltd.).

The back sheet 44 is formed of a moisture-permeable PE film (with a basis weight of 25 g/m$^2$, manufactured by Mitsui Chemicals, Inc.).

Further, numerical values in FIGS. 21A and 21B represent dimensions, and are to be read in "mm" units. Note that, the present invention is not limited to those sizes.

What is claimed is:

1. An absorbent article, comprising:
   an individual-wrapping sheet which is liquid-impermeable, the individual-wrapping sheet being used for a leak preventer at a time of wearing and for wrapping the absorbent article at a time of disposing of after wearing;
   an absorber arranged on an upper side of the individual-wrapping sheet, and capable of absorbing an aqueous liquid;
   a back-up sheet arranged between the individual-wrapping sheet and the absorber and capable of retaining the aqueous liquid; and
   an additional sheet arranged under the absorber and on the back-up sheet, the additional sheet comprising a hydrophobic non-woven fabric or a highly air-permeable and water resistant barrier sheet, wherein
   the individual-wrapping sheet comprises a single sheet that includes a first portion folded back to form a liquid-storing portion in a form of a bag which is provided at a rear portion of the individual-wrapping sheet the bag forming an internal space on the upper side of the individual-wrapping sheet at the time of wearing,
   a rear end portion of the absorber exists in the internal space formed by the liquid-storing portion, and
   the absorber is independent from the back-up sheet.

2. The absorbent article according to claim 1, wherein
   the individual-wrapping sheet includes an individual-wrapping-sheet main-body portion and a pair of wing portions existing on both right and left sides of the individual-wrapping-sheet main-body portion, the pair of wing portions being coupleable to each other on any one of an upper side and a lower side of the individual-wrapping-sheet main-body portion.

3. The absorbent article according to claim 2, wherein
   the pair of wing portions are coupleable to each other with tackifiers applied respectively to the pair of wing portions.

4. The absorbent article according to claim 2, wherein one of the pair of wing portions includes a male member and another of the pair of wing portions includes a female member so that the pair of wing portions are coupleable to each other by fitting of the male member and the female member.

5. The absorbent article according to claim 1, wherein the individual-wrapping sheet includes, on a lower-side surface thereof, a tackifier adherable to an inner surface of an underwear garment of a wearer at the time of wearing.

6. The absorbent article according to claim 1, wherein the individual-wrapping sheet includes, on a lower-side surface thereof, an anti-slip member which suppresses slipping with respect to an inner surface of an underwear garment of a wearer at the time of wearing.

7. The absorbent article according to claim 1, wherein the individual-wrapping sheet includes, on an upper-side surface thereof, a pair of side-barrier portions standing upward, the pair of side-barrier portions being provided on both right and left sides of the individual-wrapping sheet.

8. The absorbent article according to claim 1, wherein a rear end portion of the back-up sheet exists in the internal space formed by the liquid-storing portion.

9. The absorbent article according to claim 1, wherein the back-up sheet is folded back on a rear side with respect to the rear end portion of the absorber so that a rear end portion of the back-up sheet exists on an upper side of the absorber.

10. The absorbent article according to claim 1, wherein the back-up sheet is folded back on a rear side with respect to the rear end portion of the absorber and on a front side with respect to a front end portion of the liquid-storing portion of the individual-wrapping sheet so that a rear end portion of the back-up sheet exists on an upper side of the liquid-storing portion.

11. The absorbent article according to claim 1, wherein the back-up sheet is folded back on a rear side with respect to a rear end portion of the absorber and on a front side with respect to a front end portion of the liquid-storing portion of the individual-wrapping sheet so that a rear end portion of the back-up sheet exists on a rear side with respect to the liquid-storing portion.

12. The absorbent article according to claim 1, further comprising a spreading-leakage preventing sheet provided on the upper side of the absorber, the spreading-leakage preventing sheet being capable of retaining an aqueous liquid, in which a part of the spreading-leakage preventing sheet exists in the internal space of the liquid-storing portion and another part of the spreading-leakage preventing sheet is out of the internal space of the liquid-storing portion.

13. The absorbent article according to claim 12, wherein the spreading-leakage preventing sheet is folded back on a front side with respect to a front end portion of the liquid-storing portion.

14. The absorbent article according to claim 1, wherein the individual-wrapping sheet is formed of a laminated body of a liquid-impermeable sheet and a hydrophobic non-woven fabric, the hydrophobic non-woven fabric existing on an upper side and/or a lower side of the liquid-impermeable sheet.

15. The absorbent article according to claim 1, wherein at least an inner surface of the individual-wrapping sheet is formed of a liquid-impermeable sheet, and the back-up sheet is formed of a hydrophilic non-woven fabric, the liquid-impermeable sheet and the hydrophilic non-woven fabric being formed integrally with each other as a laminated body.

16. The absorbent article according to claim 1, wherein the absorbent article is an incontinence pad.

17. The absorbent article according to claim 1, wherein the absorbent article is sanitary napkin.

18. An absorbent article, comprising:
an individual-wrapping sheet which is liquid-impermeable;
an absorber arranged on an upper side of the individual-wrapping sheet, and capable of absorbing an aqueous liquid;
a back-up sheet arranged between the individual-wrapping sheet and the absorber and capable of retaining the aqueous liquid; and
an additional sheet arranged under the absorber and on the back-up sheet, the additional sheet comprising a hydrophobic non-woven fabric or a highly air-permeable and water resistant barrier sheet, wherein
the individual-wrapping sheet comprises a single sheet that includes a first portion folded back to form a liquid-storing portion in a form of a bag which is provided at a rear portion of the individual-wrapping sheet, the bag forming an internal space on the upper side of the individual-wrapping sheet at the time of wearing,
a rear end portion of the absorber exists in the internal space formed by the liquid-storing portion, and
the absorber is independent from the back-up sheet.

19. An absorbent article, comprising:
an individual-wrapping sheet which is liquid-impermeable, the individual wrapping sheet having a first surface and a second surface;
an absorber having a first surface and a second surface, the first surface of the absorber facing the first surface of the individual-wrapping sheet, the absorber being capable of absorbing an aqueous liquid;
a back-up sheet arranged between the first surface of the individual-wrapping sheet and the first surface of the absorber, the back-up sheet having a first surface facing the first surface of the absorber and a second surface facing the first surface of the individual-wrapping sheet, the back-up sheet being capable of retaining the aqueous liquid; and
an additional sheet having a first surface facing the first surface of the absorber and a second surface facing the first surface of the back-up sheet, the additional sheet comprising a hydrophobic non-woven fabric or a highly air-permeable and water resistant barrier sheet, wherein
the individual-wrapping sheet comprises a single sheet that includes a folded portion that is folded such that the first surface of the individual-wrapping sheet at the folded portion faces the first surface of the individual-wrapping sheet at an unfolded portion so as to form a liquid-storing portion in a form of a bag, which is provided at a rear portion of the individual-wrapping sheet and forms an internal space on the first surface of the individual-wrapping sheet at a time of wearing,
a rear end portion of the absorber exists in the internal space formed by the liquid-storing portion, and
the absorber is independent from the back-up sheet.

* * * * *